(12) United States Patent
Hipskind et al.

(10) Patent No.: US 8,178,528 B2
(45) Date of Patent: May 15, 2012

(54) HISTAMINE H3 RECEPTOR AGENTS, PREPARATION AND THERAPEUTIC USES

(75) Inventors: Philip Arthur Hipskind, New Palestine, IN (US); Takako Takakuwa, Indianapolis, IN (US); Cynthia Darshini Jesudason, Indianapolis, IN (US); Robert Alan Gadski, Indianapolis, IN (US); William Joseph Hornback, Fishers, IN (US); Richard Todd Pickard, Noblesville, IN (US); Lisa Selsam Beavers, Franklin, IN (US)

(73) Assignee: Eli Lilly and Company, Indianapolis, IN (US)

( * ) Notice: Subject to any disclaimer, the term of this patent is extended or adjusted under 35 U.S.C. 154(b) by 813 days.

(21) Appl. No.: 11/909,727

(22) PCT Filed: Mar. 28, 2006

(86) PCT No.: PCT/US2006/011320
§ 371 (c)(1),
(2), (4) Date: Sep. 26, 2007

(87) PCT Pub. No.: WO2006/107661
PCT Pub. Date: Oct. 12, 2006

(65) Prior Publication Data
US 2010/0160406 A1 Jun. 24, 2010

Related U.S. Application Data

(60) Provisional application No. 60/667,582, filed on Apr. 1, 2005.

(51) Int. Cl.
*A61K 31/535* (2006.01)
*A61K 31/497* (2006.01)
*A61K 31/445* (2006.01)
*C07D 413/00* (2006.01)
*C07D 409/00* (2006.01)
*C07D 207/00* (2006.01)

(52) U.S. Cl. ......... 514/235.5; 514/254.01; 514/326; 514/422; 544/141; 544/372; 546/208; 548/523

(58) Field of Classification Search .......... None
See application file for complete search history.

(56) References Cited

U.S. PATENT DOCUMENTS
2010/0048580 A1* 2/2010 Beavers et al. .......... 514/252.05

FOREIGN PATENT DOCUMENTS
| WO | WO 02/076925 | 10/2002 |
| WO | WO 03/064411 | 8/2003 |
| WO | WO 03/086398 | 10/2003 |
| WO | WO 2005/097740 | 10/2005 |
| WO | WO 2006/023462 | 3/2006 |

OTHER PUBLICATIONS

U.S. Department of Health and Human Services FDA, Guidance for Industry, Lists of Solvents (2003).*

* cited by examiner

*Primary Examiner* — Brandon Fetterolf
*Assistant Examiner* — Anna Pagonakis
(74) *Attorney, Agent, or Firm* — Dan L. Wood

(57) ABSTRACT

The present invention discloses novel compounds of Formula (I) or pharmaceutically acceptable salts thereof which have histamine—H3 receptor antagonist or inverse agonist activity, as well as methods and intermediates for preparing such compounds. In another embodiment, the invention discloses pharmaceutical compositions comprising compounds of Formula (I) as well as methods of using these compositions to treat obesity, cognitive deficiencies, narcolepsy, and other histamine H3 receptor-related diseases.

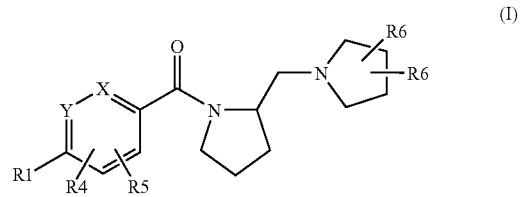

12 Claims, No Drawings

HISTAMINE H3 RECEPTOR AGENTS, PREPARATION AND THERAPEUTIC USES

This is the national phase application, under 35 USC 371, for PCT/US2006/011320, filed Mar. 28, 2006, which claims the benefit, under 35 USC 119(e), of U.S. provisional application 60/667,582 filed Apr. 1, 2005.

The present invention relates to novel substituted aryl-methanone-pyrrolidinyl-methyl-pyrrolidinyl compounds, and to the use of these compounds as pharmaceutical compositions, to pharmaceutical compositions comprising the compounds, to methods of treatment employing these compounds and compositions, and to intermediates and methods for making these compounds.

The histamine H3 receptor is relatively neuron specific and inhibits the release of a number of monoamines, including histamine. The histamine H3 receptor is a presynaptic autoreceptor and hetero-receptor located both in the central and the peripheral nervous system. The histamine H3 receptor regulates the release of histamine and other neurotransmitters, such as serotonin and acetylcholine. These are examples of histamine H3 receptor mediated responses. Recent evidence suggests that the H3 receptor shows intrinsic, constitutive activity, in vitro as well as in vivo (i.e. it is active in the absence of an agonist). Compounds acting as inverse agonists can inhibit this activity. A histamine H3 receptor antagonist or inverse agonist would therefore be expected to increase the release of H3 receptor-regulated neurotransmitters in the brain. A histamine H3 receptor agonist, on the contrary, leads to an inhibition of the biosynthesis of histamine and an inhibition of the release of histamine and also of other neurotransmitters such as serotonin and acetylcholine. These findings suggest that histamine H3 receptor agonists, inverse agonists, and antagonists could be important mediators of neuronal activity, and the activities of other cells that may express this receptor. Inverse agonism or selective antagonism of the histamine H3 receptor raises brain levels of histamine, and other monoamines, and inhibits activities such as food consumption while minimizing non-specific peripheral consequences. By this mechanism, they induce a prolonged wakefulness, improved cognitive function, reduction in food intake and normalization of vestibular reflexes. Accordingly, the histamine H3 receptor is an important target for new therapeutics in Alzheimer disease, mood and attention adjustments, cognitive deficiencies, obesity, dizziness, schizophrenia, epilepsy, sleeping disorders, narcolepsy and motion sickness.

Histamine mediates its activity via four receptor subtypes, H1R, H2R, H3R and a newly identified receptor designated GPRv53 [(Oda T., et al., J. Biol. Chem. 275 (47): 36781-6 (2000)], and alternative names for this receptor are PORT3 or H4R. Although relatively selective ligands have been developed for H1R, H2R and H3R, few specific ligands have been developed that can distinguish H3R from GPRv53. GPRv53 is a widely distributed receptor found at high levels in human leukocytes. Activation or inhibition of this receptor could result in undesirable side effects when targeting antagonism of the H3R receptor. The identification of the H4R receptor has fundamentally changed histamine biology and must be considered in the development of histamine H3 receptor antagonists.

Some histamine H3 receptor antagonists were created which resembled histamine in possessing an imidazole ring generally substituted in the 4(5) position (Ganellin et al., Ars Pharmaceutica, 1995, 36:3, 455-468). A variety of patents and patent applications directed to antagonists and agonists having such structures include EP 197840, EP 494010, WO 97/29092, WO 96/38141, and WO96/38142. These imidazole-containing compounds have the disadvantage of poor blood-brain barrier penetration, interaction with cytochrome P-450 proteins, and hepatic and ocular toxicities. Recently other imidazole and non-imidazole ligands of the histamine H3 receptor have been described, such as those in WO2002076925. The compounds of the present invention differ in structure from the compounds described in the art.

There remains a need for improved treatments using alternative or improved pharmaceutical agents that act as histamine H3 receptor agonists, inverse agonists, or antagonists, to modulate H3 receptor activity, and treat the diseases that could benefit from H3 receptor modulation. The present invention provides such a contribution to the art based on the finding that a novel class of substituted aryl-methanone-pyrrolidinyl-methyl-pyrrolidinyl compounds has a high affinity, selective, and potent activity at the histamine H3 receptor. The subject invention is distinct in the particular structures and their activities.

SUMMARY OF THE INVENTION

The present invention provides a compound structurally represented by Formula I:

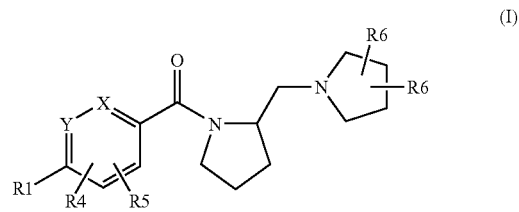

or a pharmaceutically acceptable salt thereof, wherein:
Y independently represents carbon or nitrogen;
X independently represents carbon or nitrogen, provided that at least one of Y or X is carbon;
R1 is independently
-halogen, —CN, —NO$_2$, —(C$_1$-C$_7$) alkyl(optionally substituted with 1 to 3 halogens), —(C$_3$-C$_8$) cycloalkyl, —(C$_1$-C$_7$) alkyl-S(O)$_2$—(C$_1$-C$_3$) alkyl, —(C$_1$-C$_7$) alkyl-C(O)—O—R3, —(C$_1$-C$_7$) alkyl-S(O)$_2$-phenyl(R2)(R2)(R2), —(C$_1$-C$_7$) alkyl-S—(C$_1$-C$_7$) alkyl, —(C$_1$-C$_7$) alkyl-(C$_3$-C$_8$) cycloalkyl, —(C$_1$-C$_7$) alkyl-phenyl(R2)(R2)(R2), —C(O)-phenyl(R2)(R2)(R2), —C(O)—(C$_1$-C$_7$) alkyl, —C(O)—(C$_3$-C$_8$) cycloalkyl, —(C$_1$-C$_7$) alkyl-C(O)-phenyl(R2)(R2)(R2), —S—(C$_1$-C$_7$) alkyl, —S—(C$_1$-C$_7$) alkyl-phenyl(R2)(R2)(R2), —S—(C$_3$-C$_8$) cycloalkyl-(C$_1$-C$_7$) alkyl, —S—(C$_3$-C$_8$) cycloalkyl, —S—(C$_2$-C$_7$) alkenyl, —S-phenyl(R2)(R2)(R2), —SO$_2$-phenyl(R2)(R2)(R2), —SO$_2$R7, —S(O)R7, —(C$_2$-C$_7$) alkenyl, —(C$_3$-C$_8$) cycloalkenyl, —(C$_2$-C$_7$) alkenyl-S(O)$_2$—(C$_1$-C$_3$) alkyl, —(C$_2$-C$_7$) alkenyl-C(O)—O—R3, —(C$_2$-C$_7$) alkenyl-S(O)$_2$-phenyl(R2)(R2)(R2), —(C$_2$-C$_7$) alkenyl-S—(C$_1$-C$_7$) alkyl, —(C$_2$-C$_7$) alkenyl-(C$_3$-C$_8$) cycloalkyl, or —(C$_2$-C$_7$) alkenyl-phenyl(R2)(R2)(R2);
R2 is independently at each occurrence
—H, -halogen, —(C$_1$-C$_7$) alkyl(optionally substituted with 1 to 3 halogens), —C(O)R7, —C(O)OR7, —C(O)(C$_3$-C$_8$)cycloalkyl, —OCF$_3$, —OR7, —SR7, —SO$_2$R7, —SO$_2$CF$_3$, or —S(O)R7;
R3 is independently at each occurrence
—H, or —(C$_1$-C$_3$) alkyl(optionally substituted with 1 to 3 halogens);

R4 and R5 are independently at each occurrence
—H, -halogen, —($C_1$-$C_3$) alkyl(optionally substituted with 1 to 3 halogens), or —OR3, provided that when Y is nitrogen, then R4 or R5 are not attached to Y, and provided that when X is nitrogen, then R4 or R5 are not attached to X;

R6 is independently at each occurrence
—H, -halogen, —$CF_3$, —($C_1$-$C_3$) alkyl(optionally substituted with 1 to 3 halogens), or —OR3; and R7 is independently at each occurrence
—H, —($C_1$-$C_7$) alkyl(optionally substituted with 1 to 3 halogens), or —($C_2$-$C_7$) alkenyl.

The present invention provides compounds that show a selective and high affinity binding for the histamine H3 receptor, and thus the compounds are useful as histamine H3 receptor antagonists or inverse agonists. In another aspect, the present invention provides compounds that are useful as selective antagonists or inverse agonists of the histamine H3 receptor but have little or no binding affinity of GPRv53. In addition, the present invention provides a method for the treatment of a nervous system disorder, which comprises administering to a patient in need thereof an effective amount of a compound of formula I. The present invention further provides a method for the treatment of obesity or cognitive disorders, which comprises administering to a patient in need thereof an effective amount of a compound of formula I. In yet another aspect, the present invention provides pharmaceutical compositions comprising antagonists or inverse agonists of the histamine H3 receptor.

DETAILED DESCRIPTION OF THE INVENTION

In one embodiment, the present invention provides compounds of Formula I as described in detail above. While all of the compounds of the present invention are useful, certain of the compounds are particularly interesting and are preferred.

In a preferred embodiment the present invention provides a compound structurally represented by Formula I, or a pharmaceutically acceptable salt thereof, wherein:

Y independently represents carbon; X independently represents carbon;

R1 is independently
-halogen, —CN, —$NO_2$, —($C_1$-$C_7$) alkyl(optionally substituted with 1 to 3 halogens), —($C_3$-$C_8$) cycloalkyl, —($C_1$-$C_7$) alkyl-S(O)$_2$—($C_1$-$C_3$) alkyl, —($C_1$-$C_7$) alkyl-C(O)—O—R3, —($C_1$-$C_7$) alkyl-S(O)$_2$-phenyl(R2)(R2)(R2), —($C_1$-$C_7$) alkyl-S—($C_1$-$C_7$) alkyl, —($C_1$-$C_7$) alkyl-($C_3$-$C_8$) cycloalkyl, —($C_1$-$C_7$) alkyl-phenyl(R2)(R2)(R2), —C(O)-phenyl(R2)(R2)(R2), —C(O)—($C_1$-$C_7$) alkyl, —C(O)—($C_3$-$C_8$) cycloalkyl, —($C_1$-$C_7$) alkyl-C(O)-phenyl(R2)(R2)(R2), —S—($C_1$-$C_7$) alkyl, —S—($C_1$-$C_7$) alkyl-phenyl(R2)(R2)(R2), —S—($C_3$-$C_8$) cycloalkyl-($C_1$-$C_7$) alkyl, —S—($C_3$-$C_8$) cycloalkyl, —S—($C_2$-$C_7$) alkenyl, —S-phenyl(R2)(R2)(R2), —SO$_2$-phenyl(R2)(R2)(R2), —SO$_2$R7, —S(O)R7, —($C_2$-$C_7$) alkenyl, —($C_3$-$C_8$) cycloalkenyl, —($C_2$-$C_7$) alkenyl-S(O)$_2$—($C_1$-$C_3$) alkyl, —($C_2$-$C_7$) alkenyl-C(O)—O—R3, —($C_2$-$C_7$) alkenyl-S(O)$_2$-phenyl(R2)(R2)(R2), —($C_2$-$C_7$) alkenyl-S—($C_1$-$C_7$) alkyl, —($C_2$-$C_7$) alkenyl-($C_3$-$C_8$) cycloalkyl, or —($C_2$-$C_7$) alkenyl-phenyl(R2)(R2)(R2);

R2 is independently at each occurrence
—H, -halogen, —($C_1$-$C_7$) alkyl(optionally substituted with 1 to 3 halogens), —C(O)R7, —C(O)OR7, —C(O)($C_3$-$C_8$)cycloalkyl, —OCF$_3$, —OR7, —SR7, —SO$_2$R7, —SO$_2$CF$_3$, or —S(O)R7;

R3 is independently at each occurrence
—H, or —($C_1$-$C_3$) alkyl(optionally substituted with 1 to 3 halogens);

R4 and R5 are independently at each occurrence
—H, -halogen, —($C_1$-$C_3$) alkyl(optionally substituted with 1 to 3 halogens), or —OR3, provided that when Y is nitrogen, then R4 or R5 are not attached to Y, and provided that when X is nitrogen, then R4 or R5 are not attached to X;

R6 is independently at each occurrence
—H, -halogen, —CF$_3$, —($C_1$-$C_3$) alkyl(optionally substituted with 1 to 3 halogens), or —OR3; and R7 is independently at each occurrence
—H, —($C_1$-$C_7$) alkyl(optionally substituted with 1 to 3 halogens), or —($C_2$-$C_7$) alkenyl.

In a preferred embodiment the present invention provides a compound structurally represented by Formula I, or a pharmaceutically acceptable salt thereof, wherein:

Y independently nitrogen; X independently represents carbon;

R1 is independently
-halogen, —CN, —NO$_2$, —($C_1$-$C_7$) alkyl(optionally substituted with 1 to 3 halogens), —($C_3$-$C_8$) cycloalkyl, —($C_1$-$C_7$) alkyl-S(O)$_2$—($C_1$-$C_3$) alkyl, —($C_1$-$C_7$) alkyl-C(O)—O—R3, —($C_1$-$C_7$) alkyl-S(O)$_2$-phenyl(R2)(R2)(R2), —($C_1$-$C_7$) alkyl-S—($C_1$-$C_7$) alkyl, —($C_1$-$C_7$) alkyl-($C_3$-$C_8$) cycloalkyl, —($C_1$-$C_7$) alkyl-phenyl(R2)(R2)(R2), —C(O)-phenyl(R2)(R2)(R2), —C(O)—($C_1$-$C_7$) alkyl, —C(O)—($C_3$-$C_8$) cycloalkyl, —($C_1$-$C_7$) alkyl-C(O)-phenyl(R2)(R2)(R2), —S—($C_1$-$C_7$) alkyl, —S—($C_1$-$C_7$) alkyl-phenyl(R2)(R2)(R2), —S—($C_3$-$C_8$) cycloalkyl-($C_1$-$C_7$) alkyl, —S—($C_3$-$C_8$) cycloalkyl, —S—($C_2$-$C_7$) alkenyl, —S-phenyl(R2)(R2)(R2), —SO$_2$-phenyl(R2)(R2)(R2), —SO$_2$R7, —S(O)R7, —($C_2$-$C_7$) alkenyl, —($C_3$-$C_8$) cycloalkenyl, —($C_2$-$C_7$) alkenyl-S(O)$_2$—($C_1$-$C_3$) alkyl, —($C_2$-$C_7$) alkenyl-C(O)—O—R3, —($C_2$-$C_7$) alkenyl-S(O)$_2$-phenyl(R2)(R2)(R2), —($C_2$-$C_7$) alkenyl-S—($C_1$-$C_7$) alkyl, —($C_2$-$C_7$) alkenyl-($C_3$-$C_8$) cycloalkyl, or —($C_2$-$C_7$) alkenyl-phenyl(R2)(R2)(R2);

R2 is independently at each occurrence
—H, -halogen, —($C_1$-$C_7$) alkyl(optionally substituted with 1 to 3 halogens), —C(O)R7, —C(O)OR7, —C(O)($C_3$-$C_8$)cycloalkyl, —OCF$_3$, —OR7, —SR7, —SO$_2$R7, —SO$_2$CF$_3$, or —S(O)R7;

R3 is independently at each occurrence
—H, or —($C_1$-$C_3$) alkyl(optionally substituted with 1 to 3 halogens);

R4 and R5 are independently at each occurrence
—H, -halogen, —($C_1$-$C_3$) alkyl(optionally substituted with 1 to 3 halogens), or —OR3, provided that when Y is nitrogen, then R4 or R5 are not attached to Y, and provided that when X is nitrogen, then R4 or R5 are not attached to X;

R6 is independently at each occurrence
—H, -halogen, —CF$_3$, —($C_1$-$C_3$) alkyl(optionally substituted with 1 to 3 halogens), or —OR3; and R7 is independently at each occurrence
—H, —($C_1$-$C_7$) alkyl(optionally substituted with 1 to 3 halogens), or —($C_2$-$C_7$) alkenyl.

In a preferred embodiment the present invention provides a compound structurally represented by Formula I, or a pharmaceutically acceptable salt thereof, wherein:

Y independently carbon; X independently represents nitrogen;

R1 is independently
-halogen, —CN, —NO$_2$, —($C_1$-$C_7$) alkyl(optionally substituted with 1 to 3 halogens), —($C_3$-$C_8$) cycloalkyl, —($C_1$-$C_7$) alkyl-S(O)$_2$—($C_1$-$C_3$) alkyl, —($C_1$-$C_7$) alkyl-C(O)—O—R3, —($C_1$-$C_7$) alkyl-S(O)$_2$-phenyl(R2)(R2)(R2), —($C_1$-$C_7$) alkyl-S—($C_1$-$C_7$) alkyl, —($C_1$-$C_7$) alkyl-($C_3$-$C_8$) cycloalkyl, —($C_1$-$C_7$) alkyl-phenyl(R2)(R2)(R2), —C(O)-phenyl(R2)(R2)(R2), —C(O)—($C_1$-$C_7$) alkyl, —C(O)—($C_3$-$C_8$) cycloalkyl, —($C_1$-$C_7$) alkyl-C(O)-phenyl(R2)(R2)(R2), —S—($C_1$-$C_7$) alkyl, —S—($C_1$-$C_7$) alkyl-phenyl(R2)(R2)(R2), —S—($C_3$-$C_8$) cycloalkyl-($C_1$-$C_7$) alkyl, —S—($C_3$-$C_8$) cycloalkyl, —S—($C_2$-$C_7$) alkenyl, —S-phenyl(R2)(R2)(R2), —SO$_2$-phenyl(R2)(R2)(R2), —SO$_2$R7, —S(O)R7, —($C_2$-$C_7$) alkenyl, —($C_3$-$C_8$) cycloalkenyl, —($C_2$-$C_7$) alkenyl-S(O)$_2$—($C_1$-$C_3$) alkyl, —($C_2$-$C_7$) alkenyl-C(O)—O—R3, —($C_2$-$C_7$) alkenyl-S(O)$_2$-phenyl(R2)(R2)(R2), —($C_2$-$C_7$) alkenyl-S—($C_1$-$C_7$) alkyl, —($C_2$-$C_7$) alkenyl-($C_3$-$C_8$) cycloalkyl, or —($C_2$-$C_7$) alkenyl-phenyl(R2)(R2)(R2);

R2 is independently at each occurrence
—H, -halogen, —($C_1$-$C_7$) alkyl(optionally substituted with 1 to 3 halogens), —C(O)R7, —C(O)OR7, —C(O)($C_3$-$C_8$)cycloalkyl, —OCF$_3$, —OR7, —SR7, —SO$_2$R7, —SO$_2$CF$_3$, or —S(O)R7;

R3 is independently at each occurrence
—H, or —($C_1$-$C_3$) alkyl(optionally substituted with 1 to 3 halogens);

R4 and R5 are independently at each occurrence
—H, -halogen, —($C_1$-$C_3$) alkyl(optionally substituted with 1 to 3 halogens), or —OR3, provided that when Y is nitrogen, then R4 or R5 are not attached to Y, and provided that when X is nitrogen, then R4 or R5 are not attached to X;

R6 is independently at each occurrence
—H, -halogen, —CF$_3$, —($C_1$-$C_3$) alkyl(optionally substituted with 1 to 3 halogens), or —OR3; and R7 is independently at each occurrence
—H, —($C_1$-$C_7$) alkyl(optionally substituted with 1 to 3 halogens), or —($C_2$-$C_7$) alkenyl.

In a preferred embodiment the present invention provides a compound structurally represented by Formula I, or a pharmaceutically acceptable salt thereof, wherein:

Y independently represents carbon or nitrogen; X independently represents carbon or nitrogen, provided that at least one of Y or X is carbon;

R1 is independently
-halogen, —CN, —NO$_2$, —($C_1$-$C_7$) alkyl(optionally substituted with 1 to 3 halogens), —($C_3$-$C_8$) cycloalkyl, —($C_1$-$C_7$) alkyl-S(O)$_2$—($C_1$-$C_3$) alkyl, —($C_1$-$C_7$) alkyl-phenyl(R2)(R2)(R2), —C(O)-phenyl(R2)(R2)(R2), —C(O)—($C_1$-$C_7$) alkyl, —C(O)—($C_3$-$C_8$) cycloalkyl, —($C_1$-$C_7$) alkyl-C(O)-phenyl(R2)(R2)(R2), —S—($C_1$-$C_7$) alkyl, —S—($C_1$-$C_7$) alkyl-phenyl(R2)(R2)(R2), —S—($C_3$-$C_8$) cycloalkyl-($C_1$-$C_7$) alkyl, —S—($C_3$-$C_8$) cycloalkyl, —S-phenyl(R2)(R2)(R2), —SO$_2$-phenyl(R2)(R2)(R2), —SO$_2$R7, or —S(O)R7;

R2 is independently at each occurrence
—H, -halogen, —($C_1$-$C_3$) alkyl(optionally substituted with 1 to 3 halogens), —C(O)R7, —C(O)OR7, —OCF$_3$, —OR7, —SR7, —SO$_2$R7, —SO$_2$CF$_3$, or —S(O)R7;

R3 is independently at each occurrence
—H, or —($C_1$-$C_3$) alkyl(optionally substituted with 1 to 3 halogens);

R4 is H or -halogen; R5 is H or halogen,
provided that when Y is nitrogen, then R4 or R5 are not attached to Y, and provided that when X is nitrogen, then R4 or R5 are not attached to X;

R6 is H at one occurrence, and R6 is —CH$_3$ at the second occurrence; and

R7 is independently at each occurrence
—H or —($C_1$-$C_3$) alkyl(optionally substituted with 1 to 3 halogens).

Other embodiments of the invention are provided wherein each of the embodiments described herein above is further narrowed as described in the following preferences. Specifically, each of the preferences below is independently combined with each of the embodiments above, and the particular combination provides another embodiment in which the variable indicated in the preference is narrowed according to the preference. Further, the invention provides a pharmaceutical composition comprising the compounds of the new embodiments created by the combinations of the embodiments described herein above with the narrowing preferences below, and a pharmaceutically acceptable carrier.

Preferably Y is carbon. Preferably Y is nitrogen. Preferably X is carbon. Preferably X is nitrogen.

Preferably R1 is -halogen, —($C_1$-$C_7$) alkyl(optionally substituted with 1 to 3 halogens), —($C_3$-$C_8$) cycloalkyl, —($C_1$-$C_7$) alkyl-S(O)$_2$—($C_1$-$C_3$) alkyl, —($C_1$-$C_7$) alkyl-C(O)—O—R3, —($C_1$-$C_7$) alkyl-S—($C_1$-$C_7$) alkyl, —($C_1$-$C_7$) alkyl-($C_3$-$C_8$) cycloalkyl, —C(O)—($C_1$-$C_7$) alkyl, —S—($C_1$-$C_7$) alkyl, —S(O)R7, —C(O)—($C_3$-$C_8$) cycloalkyl, —S—($C_3$-$C_8$) cycloalkyl-($C_1$-$C_7$) alkyl, or —S—($C_3$-$C_8$) cycloalkyl.

Preferably R1 is —($C_1$-$C_7$) alkyl-S(O)$_2$-phenyl(R2)(R2)(R2), —($C_1$-$C_7$) alkyl-phenyl(R2)(R2)(R2), —C(O)-phenyl(R2)(R2)(R2), —($C_1$-$C_7$) alkyl-C(O)-phenyl(R2)(R2)(R2), —S—($C_1$-$C_7$) alkyl-phenyl(R2)(R2)(R2), —S-phenyl(R2)(R2), —SO$_2$-phenyl(R2)(R2)(R2), or —SO$_2$R7.

Preferably R1 is -halogen. Preferably R1 is —($C_1$-$C_7$) alkyl(optionally substituted with 1 to 3 halogens), —($C_3$-$C_8$) cycloalkyl, or —($C_1$-$C_7$) alkyl-($C_3$-$C_8$) cycloalkyl.

Preferably R2 is independently at each occurrence —H, -halogen, —($C_1$-$C_7$) alkyl(optionally substituted with 1 to 3 halogens), —C(O)R7, —C(O)OR7, —OCF$_3$, —OR7, —SR7, —SO$_2$R7, —SO$_2$CF$_3$, or —S(O)R7.

Preferably R2 is independently at each occurrence —H, -halogen, or —($C_1$-$C_3$)alkyl (optionally substituted with 1 to 3 halogens). Preferably R2 is independently at each occurrence —H.

Preferably R4 and R5 are independently at each occurrence —H. Preferably R4 and R5 are independently at each occurrence —H or -halogen. Preferably R4 and R5 are independently at each occurrence -halogen or —($C_1$-$C_3$) (alkyl optionally substituted with 1 to 3 halogens). Preferably R4 is hydrogen and R5 is halogen.

Preferably R6 is independently at each occurrence —H. Preferably R6 is independently at each occurrence —H or —($C_1$-$C_3$) alkyl (optionally substituted with 1 to 3 halogens). Preferably R6 is independently at each occurrence —H or —CH$_3$ (optionally substituted with 1 to 3 halogens). Preferably one occurrence of R6 is —H and the second occurrence of R6 is —CH$_3$ (optionally substituted with 1 to 3 halogens). Preferably one occurrence of R6 is —H and the second occurrence of R6 is —CH$_3$.

Preferably R7 is independently at each occurrence —H, or —($C_1$-$C_3$) alkyl(optionally substituted with 1 to 3 halogens).

In another embodiment, the present invention is a compound structurally represented by Formula I:

(I)

[Chemical structure showing formula I with R1, R4, R5, R6, X, Y, O groups]

or a pharmaceutically acceptable salt thereof wherein:
Y independently represents carbon or nitrogen,
X independently represents carbon or nitrogen, provided that at least one of Y or X is carbon,
R1 is independently
-halogen, —CN, —NO$_2$, —(C$_1$-C$_7$) alkyl, —(C$_3$-C$_8$) cycloalkyl, —(C$_1$-C$_7$) alkyl-S(O)$_2$—(C$_1$-C$_3$) alkyl, —(C$_1$-C$_7$) alkyl-C(O)—O—R3, —(C$_1$-C$_7$) alkyl-S(O)$_2$-phenyl(R2)(R2)(R2), —(C$_1$-C$_7$) alkyl-S—(C$_1$-C$_7$) alkyl, —(C$_1$-C$_7$) alkyl-(C$_3$-C$_8$) cycloalkyl, —(C$_1$-C$_7$) alkyl-phenyl(R2)(R2)(R2), —C(O)-phenyl(R2)(R2)(R2), —C(O)—(C$_1$-C$_7$) alkyl, —C(O)—(C$_3$-C$_8$) cycloalkyl, —(C$_1$-C$_7$) alkyl-C(O)-phenyl(R2)(R2)(R2), —S—(C$_1$-C$_7$) alkyl, —S—(C$_1$-C$_7$) alkyl-phenyl(R2)(R2)(R2), —S—(C$_3$-C$_8$) cycloalkyl-(C$_1$-C$_7$) alkyl, —S—(C$_3$-C$_8$) cycloalkyl, —S—(C$_2$-C$_7$) alkenyl, —S-phenyl(R2)(R2)(R2), —SO$_2$-phenyl(R2)(R2)(R2), —SO$_2$R7, —S(O)R7, —(C$_2$-C$_7$) alkenyl, —(C$_3$-C$_8$) cycloalkenyl, —(C$_2$-C$_7$) alkenyl-S(O)$_2$—(C$_1$-C$_3$) alkyl, —(C$_2$-C$_7$) alkenyl-C(O)—O—R3, —(C$_2$-C$_7$) alkenyl-S(O)$_2$-phenyl(R2)(R2)(R2), —(C$_2$-C$_7$) alkenyl-S—(C$_1$-C$_7$) alkyl, —(C$_2$-C$_7$) alkenyl-(C$_3$-C$_8$) cycloalkyl, or —(C$_2$-C$_7$) alkenyl-phenyl(R2)(R2)(R2),
R2 is independently at each occurrence
—H, -halogen, —(C$_1$-C$_7$) alkyl, —C(O)R7, —C(O)OR7, —C(O)(C$_3$-C$_8$)cycloalkyl, —OCF$_3$, —OR7, —SR7, —SO$_2$R7, —SO$_2$CF$_3$, or —S(O)R7,
R3 is independently at each occurrence;
—H, or —(C$_1$-C$_3$) alkyl,
R4 and R5 are independently at each occurrence
—H, -halogen, —(C$_1$-C$_3$) alkyl, or —OR3, provided that when Y is nitrogen, then R4 or R5 are not attached to Y, and provided that when X is nitrogen, then R4 or R5 are not attached to X,
R6 is independently at each occurrence
—H, -halogen, —CF$_3$, —(C$_1$-C$_3$) alkyl, or —OR3,
R7 is independently at each occurrence
—H, —(C$_1$-C$_7$) alkyl, or —(C$_2$-C$_7$) alkenyl.

In one embodiment, the present invention provides compounds of Formula I as described in detail above. While all of the compounds of the present invention are useful, certain of the compounds are particularly interesting and are preferred. The following listing sets out several groups of preferred compounds. It will be understood that each of the listings may be combined with other listings to create additional groups of preferred embodiments. Other embodiments are, 1. wherein Y is carbon,
2. wherein Y is nitrogen,
3. wherein X is carbon,
4. wherein X is nitrogen,
5. wherein both Y and X are carbon,
6. wherein R1 is -halogen, —CN, —NO$_2$, —(C$_1$-C$_7$) alkyl, —(C$_3$-C$_8$) cycloalkyl, —(C$_1$-C$_7$) alkyl-S(O)$_2$—(C$_1$-C$_3$) alkyl, —(C$_1$-C$_7$) alkyl-C(O)—O—R3, —(C$_1$-C$_7$) alkyl-S(O)$_2$-phenyl(R2)(R2)(R2), —(C$_1$-C$_7$) alkyl-S—(C$_1$-C$_7$) alkyl, —(C$_1$-C$_7$) alkyl-(C$_3$-C$_8$) cycloalkyl, —(C$_1$-C$_7$) alkyl-phenyl(R2)(R2)(R2), —C(O)-phenyl(R2)(R2)(R2), —C(O)—(C$_1$-C$_7$) alkyl, —C(O)—(C$_3$-C$_8$) cycloalkyl, —(C$_1$-C$_7$) alkyl-C(O)-phenyl(R2)(R2)(R2), —S—(C$_1$-C$_7$) alkyl, —S—(C$_1$-C$_7$) alkyl-phenyl(R2)(R2)(R2), —S—(C$_3$-C$_8$) cycloalkyl-(C$_1$-C$_7$) alkyl, —S—(C$_3$-C$_8$) cycloalkyl, —S—(C$_2$-C$_7$) alkenyl, —S-phenyl(R2)(R2)(R2), —SO$_2$-phenyl(R2)(R2)(R2), —SO$_2$R7, —S(O)R7, —(C$_2$-C$_7$) alkenyl, —(C$_3$-C$_8$) cycloalkenyl, —(C$_2$-C$_7$) alkenyl-S(O)$_2$—(C$_1$-C$_3$) alkyl, —(C$_2$-C$_7$) alkenyl-C(O)—O—R3, —(C$_2$-C$_7$) alkenyl-S(O)$_2$-phenyl(R2)(R2)(R2), —(C$_2$-C$_7$) alkenyl-S—(C$_1$-C$_7$) alkyl, —(C$_2$-C$_7$) alkenyl-(C$_3$-C$_8$) cycloalkyl, or —(C$_2$-C$_7$) alkenyl-phenyl(R2)(R2)(R2),
7. wherein R1 is -halogen, —CN, —NO$_2$, —(C$_1$-C$_7$) alkyl, —(C$_3$-C$_8$) cycloalkyl, —(C$_1$-C$_7$) alkyl-S(O)$_2$—(C$_1$-C$_3$) alkyl, —(C$_1$-C$_7$) alkyl-C(O)—O—R3, —(C$_1$-C$_7$) alkyl-S(O)$_2$-phenyl(R2)(R2)(R2), —(C$_1$-C$_7$) alkyl-S—(C$_1$-C$_7$) alkyl, —(C$_1$-C$_7$) alkyl-(C$_3$-C$_8$) cycloalkyl, —(C$_1$-C$_7$) alkyl-phenyl(R2)(R2)(R2), —C(O)-phenyl(R2)(R2)(R2), —C(O)—(C$_1$-C$_7$) alkyl, —C(O)—(C$_3$-C$_8$) cycloalkyl, —(C$_1$-C$_7$) alkyl-C(O)-phenyl(R2)(R2)(R2), —S—(C$_1$-C$_7$) alkyl, —S—(C$_1$-C$_7$) alkyl-phenyl(R2)(R2)(R2), —S—(C$_3$-C$_8$) cycloalkyl-(C$_1$-C$_7$) alkyl, —S—(C$_3$-C$_8$) cycloalkyl, —S—(C$_2$-C$_7$) alkenyl, —S-phenyl(R2)(R2)(R2), —SO$_2$-phenyl(R2)(R2)(R2), —SO$_2$R7, or —S(O)R7,
8. wherein R1 is -halogen, —CN, —NO$_2$, —(C$_1$-C$_7$) alkyl, —(C$_3$-C$_8$) cycloalkyl, —(C$_1$-C$_7$) alkyl-S(O)$_2$—(C$_1$-C$_3$) alkyl, —(C$_1$-C$_7$) alkyl-C(O)—O—R3, —(C$_1$-C$_7$) alkyl-S(O)$_2$-phenyl(R2)(R2)(R2), —(C$_1$-C$_7$) alkyl-S—(C$_1$-C$_7$) alkyl, —(C$_1$-C$_7$) alkyl-(C$_3$-C$_8$) cycloalkyl, —(C$_1$-C$_7$) alkyl-phenyl(R2)(R2)(R2), —C(O)-phenyl(R2)(R2)(R2), —C(O)—(C$_1$-C$_7$) alkyl, —C(O)—(C$_3$-C$_8$) cycloalkyl, or —(C$_1$-C$_7$) alkyl-C(O)-phenyl(R2)(R2)(R2),
9. wherein R1 is —S—(C$_1$-C$_7$) alkyl, —S—(C$_1$-C$_7$) alkyl-phenyl(R2)(R2)(R2), —S—(C$_3$-C$_8$) cycloalkyl-(C$_1$-C$_7$) alkyl, —S—(C$_3$-C$_8$) cycloalkyl, —S—(C$_2$-C$_7$) alkenyl, —S-phenyl(R2)(R2)(R2), —SO$_2$-phenyl(R2)(R2)(R2), —SO$_2$R7, or —S(O)R7,
10. wherein R1 is —(C$_2$-C$_7$) alkenyl, —(C$_3$-C$_8$) cycloalkenyl, —(C$_2$-C$_7$) alkenyl-S(O)$_2$—(C$_1$-C$_3$) alkyl, —(C$_2$-C$_7$) alkenyl-C(O)—O—R3, —(C$_2$-C$_7$) alkenyl-S(O)$_2$-phenyl(R2)(R2)(R2), —(C$_2$-C$_7$) alkenyl-S—(C$_1$-C$_7$) alkyl, —(C$_2$-C$_7$) alkenyl-(C$_3$-C$_8$) cycloalkyl, or —(C$_2$-C$_7$) alkenyl-phenyl(R2)(R2)(R2),
11. wherein R2 is —H, -halogen, —(C$_1$-C$_7$) alkyl, —C(O)R7, —C(O)OR7, —C(O)(C$_3$-C$_8$)cycloalkyl, —OCF$_3$, —OR7, —SR7, —SO$_2$R7, —SO$_2$CF$_3$, or —S(O)R7,
12. wherein one independent occurrence of R2 is —H, -halogen, —(C$_1$-C$_7$) alkyl, —C(O)R7, —C(O)OR7, —C(O)(C$_3$-C$_8$)cycloalkyl, —OCF$_3$, —OR7, —SR7, —SO$_2$R7, —SO$_2$CF$_3$, or —S(O)R7, and a second independent occurrence of R2 is —H, -halogen, or —(C$_1$-C$_7$) alkyl, and a third independent occurrence of R2 is —H or -halogen,
13. wherein one independent occurrence of R2 is —SO$_2$R7, —SO$_2$CF$_3$, or —S(O)R7, and a second independent occurrence of R2 is —H, -halogen, or —(C$_1$-C$_7$) alkyl, and a third independent occurrence of R2 is —H or -halogen,
14. wherein R3 is —H, or —(C$_1$-C$_3$) alkyl,
15. wherein R3 is —(C$_1$-C$_3$) alkyl,
16. wherein R4 and R5 are independently H, -halogen, —(C$_1$-C$_3$) alkyl, or, —OR3, provided that when Y is nitrogen, then R4 or R5 are not attached to Y, and provided that when X is nitrogen, then R4 or R5 are not attached to X, 17. wherein R4 is independently -halogen,
18. wherein R4 is independently halogen and R5 is halogen,
19. wherein R6 is independently at each occurrence —H, -halogen, —$CF_3$, —($C_1$-$C_3$) alkyl, or —OR3,
20. wherein one independent occurrence of R6 is —($C_1$-$C_3$) alkyl,
21. wherein one independent occurrence of R6 is —$CH_3$,
22. wherein R7 is independently at each occurrence —H, —($C_1$-$C_7$) alkyl, or —($C_2$-$C_7$) alkenyl,
23. wherein R7 is independently at each occurrence —($C_1$-$C_7$) alkyl.

Due to their interaction with the histamine H3 receptor, the present compounds are useful in the treatment of a wide range of conditions and disorders in which an interaction with the histamine H3 receptor is beneficial. The present invention also provides a pharmaceutical composition which comprises a compound of Formula I or a pharmaceutical salt thereof, and a pharmaceutically acceptable carrier, diluent, or excipient. The present invention further provides an antagonist or inverse agonist of Formula I which is characterized by having little or no binding affinity for the histamine receptor GPRv53. The present invention further provides an antagonist or inverse agonist of Formula I which is characterized by having greater affinity for the histamine H3 receptor as compared to the affinity for the histamine H1R, H2R, or H4R receptors. The uses and methods of this invention encompass a prophylactic and therapeutic administration of a compound of Formula I, or pharmaceutical composition which comprises a compound of Formula I or a pharmaceutical salt thereof. In addition the embodiments of the present invention include the synthesis of the examples named herein by methods included herein, and supplemented by methods known in the art, to create positron emission topography (PET) ligands that bind to histamine H3 receptors and are useful for PET imaging.

Thus, the invention provides a compound of Formula I, or a pharmaceutical salt thereof, or a pharmaceutical composition which comprises a compound of Formula I, or a pharmaceutical salt thereof, for use to prevent, treat and/or alleviate diseases or conditions, for example, of the central nervous system, the peripheral nervous system, the cardiovascular system, the pulmonary system, the gastrointestinal system and the endocrinological system, while reducing and or eliminating one or more of the unwanted side effects associated with the current treatments. Such diseases or conditions include those responsive to the modulation of histamine H3 receptors, such as nervous system disorders, which include but are not limited to obesity; eating disorders, cognitive disorders, attention deficit disorders, memory processes, dementia and cognition disorders such as Alzheimer's disease and attention-deficit hyperactivity disorder; bipolar disorder, cognitive enhancement, cognitive deficits in psychiatric disorders, deficits of memory, deficits of learning, dementia, mild cognitive impairment, migraine, mood and attention alteration, motion sickness, narcolepsy, neurogenic inflammation, obsessive compulsive disorder, Parkinson's disease, schizophrenia, depression, epilepsy, and seizures or convulsions; sleep disorders such as narcolepsy; vestibular dysfunction such as Meniere's disease, migraine, motion sickness, pain, drug abuse, depression, epilepsy, jet lag, wakefulness, Tourette's syndrome, vertigo, and the like, as well as cardiovascular disorders such as acute myocardial infarction; cancer such as cutaneous carcinoma, medullary thyroid carcinoma and melanoma; respiratory disorders such as asthma; gastrointestinal disorders, inflammation, and septic shock, diabetes, type II diabetes, insulin resistance syndrome, metabolic syndrome, polycystic ovary syndrome, Syndrome X, and the like. In addition, the compounds of Formula I, or a pharmaceutical salts thereof, or a pharmaceutical composition which comprises a compound of Formula I, or a pharmaceutical salt thereof, can be useful in the treatment or prevention of a disorder or disease in which modulation of histamine H3 receptor activity has a beneficial effect. In yet another aspect, the present invention provides compounds, pharmaceutical compositions, and methods useful in the treatment of nervous system and other disorders associated with histamine H3 receptor.

In addition, the present invention provides a compound of Formula I, or a pharmaceutical salt thereof, or a pharmaceutical composition which comprises a compound of Formula I, or a pharmaceutical salt thereof, and a pharmaceutically acceptable carrier, diluent, or excipient; for use in inhibiting the histamine H3 receptor; for use in inhibiting a histamine H3 receptor mediated cellular response in a mammal; for use to increase the release of H3 receptor-regulated neurotransmitters in a mammal; for use in treating a disease arising from excessive histamine H3 receptor activity.

The present invention is further related to the use of a compound of Formula I, or a pharmaceutical salt thereof, or a pharmaceutical composition which comprises a compound of Formula I, or a pharmaceutical salt thereof, and a pharmaceutically acceptable carrier, diluent, or excipient; for the manufacture of a medicament for inhibiting the histamine H3 receptor; for the manufacture of a medicament for inhibiting a histamine H3 receptor mediated cellular response in a mammal; for the manufacture of a medicament to increase the release of H3 receptor-regulated neurotransmitters in the brain of a mammal; for the manufacture of a medicament for treating a disease arising from excessive histamine H3 receptor activity; for the manufacture of a medicament for treating cognitive disorders in a mammal; and for the manufacture of a medicament for treating nervous system disorders in a mammal including but not limited to obesity, cognitive disorders, attention deficit disorders, memory processes, dementia and cognition disorders such as Alzheimer's disease and attention-deficit hyperactivity disorder; bipolar disorder, cognitive enhancement, cognitive deficits in psychiatric disorders, deficits of memory, deficits of learning, dementia, mild cognitive impairment, migraine, mood and attention alteration, motion sickness, narcolepsy, neurogenic inflammation, obsessive compulsive disorder, Parkinson's disease, schizophrenia, depression, epilepsy, and seizures or convulsions; sleep disorders such as narcolepsy; vestibular dysfunction such as Meniere's disease, migraine, motion sickness, pain, drug abuse, depression, epilepsy, jet lag, wakefulness, Tourette's syndrome, and vertigo.

In addition, the present invention provides; a method of treating conditions resulting from excessive histamine H3 receptor activity in a mammal; a method of inhibiting the histamine H3 receptor activity in a mammal; a method of inhibiting a histamine H3 receptor mediated cellular response in a mammal; a method to increase the release of H3 receptor-regulated neurotransmitters in the brain of a mammal; a method of treating cognitive disorders in a mammal; a method of treating nervous system disorders in a mammal including but not limited to obesity, cognitive disorders, attention and attention deficit disorders, memory processes, learning, dementia, Alzheimer's disease, attention-deficit hyperactivity disorder, Parkinson's disease, schizophrenia, depression, epilepsy, and seizures or convulsions; comprising administering to a mammal in need of such treatment a histamine H3 receptor-inhibiting amount of a compound of Formula I, or a pharmaceutically acceptable salt thereof, or a pharmaceutical composition which comprises a compound of Formula I, or a pharmaceutical salt thereof, and a pharmaceutically acceptable carrier, diluent, or excipient.

The invention further provides a method of selectively increasing histamine levels in cells, or increasing histamine release by cells, by contacting the cells with an antagonist or inverse agonist of the histamine H3 receptor, the antagonist or inverse agonist being a compound of Formula I, or a pharmaceutical composition comprising a compound of Formula I, or a pharmaceutical salt thereof, and a pharmaceutically acceptable carrier, diluent, or excipient. The present invention further provides a method of treating conditions resulting from excessive histamine H3 receptor activity in a mammal comprising administering to a mammal in need of such treatment a histamine H3 receptor inhibiting amount of a pharmaceutical composition which comprises a compound of Formula I, or a pharmaceutical salt thereof, and a pharmaceutically acceptable carrier, diluent, or excipient. In addition, a compound of Formula I, or a pharmaceutical composition comprising a compound of Formula I, or a pharmaceutical salt thereof, can be useful in the treatment or prevention of a disorder or disease in which modulation of histamine H3 receptor activity has a beneficial effect.

General terms used in the description of compounds, compositions, and methods herein described, bear their usual meanings. Throughout the instant application, the following terms have the indicated meanings:

The term "GPRv53" means a recently identified novel histamine receptor as described in Oda, et al., supra. Alternative names for this receptor are PORT3 or H4R.

The term "H3R" means the histamine H3 receptor that inhibits the release of a number of monoamines, including histamine.

The term "H1R" means the histamine H1 receptor subtype.
The term "H2R" means the histamine H2 receptor subtype.
The term "H3R antagonists" is defined as a compound with the ability to block forskolin-stimulated cAMP production in response to agonist R-(−)α methylhistamine. The term "H3R inverse agonist" is defined as a compound with the ability to inhibit the constitutive activity of H3R. "Selective H3R antagonists or inverse agonists" means a compound of the present invention having a greater affinity for H3 histamine receptor than for GPRv53 histamine receptor.

In the general formulae of the present document, the general chemical terms have their usual meanings. For example;

The terms "$C_1$-$C_3$ alkyl" and "$C_1$-$C_7$ alkyl" mean hydrocarbon chains of the indicated number of carbon atoms, such as methyl, ethyl, propyl, butyl, pentyl, hexyl, heptyl, and the like, and branched or isomeric forms thereof, and as herein defined optionally may be substituted with up to four halogens, such as trifluoromethyl and the like.

"($C_3$-$C_8$) cycloalkyl" means a ring of the indicated number of carbon atoms, with three to eight carbon atoms, such as cyclopropyl, cyclobutyl, cyclopentyl and cyclohexyl, cycloheptyl, and the like, and as herein defined optionally may be substituted with up to four halogens.

"($C_2$-$C_7$) alkenyl" means hydrocarbon chains of the indicated number of carbon atoms, of either a straight or branched configuration, having at least one carbon-carbon double bond which may occur at any point along the chain, such as ethenyl, propenyl, butenyl, pentenyl, vinyl, 2-butenyl and the like, and may be optionally substituted with up to four halogens.

The term "($C_3$-$C_8$) cycloalkenyl" refers to a partially saturated carbocycle containing one or more rings of from 3 to 8 carbon atoms, such as cyclopropenyl, cyclobutenyl, cyclopentenyl, cyclohexenyl, cycloheptenyl, cyclooctenyl, and the like, optionally substituted with up to four halogens.

The substituent "-phenyl(R2)(R2)(R2)" represents a phenyl ring which is itself independently substituted three times with R2, each at any open position around the phenyl ring, and in any order.

"Boc" or "BOC" refer to t-butyl carbamate. "HOBt" is 1-hydrobenzotriazole. "PS-Trisamine" is Tris-(2-aminoethyl)amine polystyrene. "PS-Carbodiimide" or "PS-CDI" is N-Cyclohexylcarbodiimide-N'-propyloxymethyl polystyrene. "PS-DIEA" is N,N-(Diisopropyl)aminomethylpolystyrene (1% inorganic antistatic agent). "PS-DMAP" is N-(methylpolystyrene)-4-(methylamino) pyridine.

"Halogen" or "halo" means fluoro, chloro, bromo, and iodo.

"Composition" means a pharmaceutical composition and is intended to encompass a pharmaceutical product comprising the active ingredient(s) of Formula I, or X1 to X34, and the inert ingredient(s) that make up the carrier. Accordingly, the pharmaceutical compositions of the present invention encompass any composition made by admixing a compound of the present invention and a pharmaceutically acceptable carrier.

The term "unit dosage form" means physically discrete units suitable as unitary dosages for human subjects and other non-human animals, each unit containing a predetermined quantity of active material calculated to produce the desired therapeutic effect, in association with a suitable pharmaceutical carrier.

The terms "treating" and "treat", as used herein, include their generally accepted meanings, i.e., preventing, prohibiting, restraining, alleviating, ameliorating, slowing, stopping, or reversing the progression or severity of a pathological condition, described herein.

The invention includes tautomers, enantiomers and other stereoisomers of the compounds also. Thus, as one skilled in the art knows, certain aryls may exist in tautomeric forms. Such variations are contemplated to be within the scope of the invention. It will be understood that, as used herein, references to the compounds of Formula I are meant to also include the pharmaceutical salts, its enantiomers and racemic mixtures thereof.

As used herein, the term "stereoisomer" refers to a compound made up of the same atoms bonded by the same bonds but having different three-dimensional structures which are not interchangeable. The three-dimensional structures are called configurations. As used herein, the term "enantiomer" refers to two stereoisomers whose molecules are nonsuperimposable mirror images of one another. The term "chiral center" refers to a carbon atom to which four different groups are attached. As used herein, the term "diastereomers" refers to stereoisomers which are not enantiomers. In addition, two diastereomers which have a different configuration at only one chiral center are referred to herein as "epimers." The terms "racemate," "racemic mixture" or "racemic modification" refer to a mixture of equal parts of enantiomers.

The term "enantiomeric enrichment" as used herein refers to the increase in the amount of one enantiomer as compared to the other. A convenient method of expressing the enantiomeric enrichment achieved is the concept of enantiomeric excess, or "ee," which is found using the following equation:

$$ee = \frac{E^1 - E^2}{E^1 + E^2} \times 100$$

wherein $E^1$ is the amount of the first enantiomer and $E^2$ is the amount of the second enantiomer. Thus, if the initial ratio of the two enantiomers is 50:50, such as is present in a racemic mixture, and an enantiomeric enrichment sufficient to produce a final ratio of 70:30 is achieved, the ee with respect to the first enantiomer is 40%. However, if the final ratio is 90:10, the ee with respect to the first enantiomer is 80%. An ee of greater than 90% is preferred, an ee of greater than 95% is most preferred and an ee of greater than 99% is most especially preferred. Enantiomeric enrichment is readily determined by one of ordinary skill in the art using standard techniques and procedures, such as gas or high performance liquid chromatography with a chiral column. Choice of the appropriate chiral column, eluent and conditions necessary to effect separation of the enantiomeric pair is well within the knowledge of one of ordinary skill in the art. In addition, the specific stereoisomers and enantiomers of compounds of Formula I can be prepared by one of ordinary skill in the art utilizing well known techniques and processes, such as those disclosed by J. Jacques, et al., "*Enantiomers, Racemates, and Resolutions*," John Wiley and Sons, Inc., 1981, and E. L. Eliel and S. H. Wilen, "*Stereochemistry of Organic Compounds*," (Wiley-Interscience 1994), and European Patent Application No. EP-A-838448, published Apr. 29, 1998. Examples of resolutions include recrystallization techniques or chiral chromatography.

Some of the compounds of the present invention have one or more chiral centers and may exist in a variety of stereoisomeric configurations. As a consequence of these chiral centers, the compounds of the present invention occur as racemates, mixtures of enantiomers and as individual enantiomers, as well as diastereomers and mixtures of diastereomers. All such racemates, enantiomers, and diastereomers are within the scope of the present invention.

The terms "R" and "S" are used herein as commonly used in organic chemistry to denote specific configuration of a chiral center. The term "R" (rectus) refers to that configuration of a chiral center with a clockwise relationship of group priorities (highest to second lowest) when viewed along the bond toward the lowest priority group. The term "S" (sinister) refers to that configuration of a chiral center with a counterclockwise relationship of group priorities (highest to second lowest) when viewed along the bond toward the lowest priority group. The priority of groups is based upon their atomic number (in order of decreasing atomic number). A partial list of priorities and a discussion of stereochemistry is contained in "Nomenclature of Organic Compounds: Principles and Practice", (J. H. Fletcher, et al., eds., 1974) at pages 103-120.

The designation " ◄ "refers to a bond that protrudes forward out of the plane of the page. The designation " ⦀ "refers to a bond that protrudes backward out of the plane of the page. The designation " ∿ "refers to a bond wherein the stereochemistry is not defined.

In general, the term "pharmaceutical" when used as an adjective means substantially non-toxic to living organisms. For example, the term "pharmaceutical salt" as used herein, refers to salts of the compounds of Formula I which are substantially non-toxic to living organisms. See, e.g., Berge, S. M, Bighley, L. D., and Monkhouse, D. C., "Pharmaceutical Salts," *J. Pharm. Sci.*, 66:1, 1977. Typical pharmaceutical salts include those salts prepared by reaction of the compounds of Formula I with an inorganic or organic acid or base. Such salts are known as acid addition or base addition salts respectively. These pharmaceutical salts frequently have enhanced solubility characteristics compared to the compound from which they are derived, and thus are often more amenable to formulation as liquids or emulsions.

The term "acid addition salt" refers to a salt of a compound of Formula I prepared by reaction of a compound of Formula I with a mineral or organic acid. For exemplification of pharmaceutical acid addition salts see, e.g., Berge, S. M, Bighley, L. D., and Monkhouse, D. C., *J. Pharm. Sci.*, 66:1, 1977. Since compounds of this invention can be basic in nature, they accordingly react with any of a number of inorganic and organic acids to form pharmaceutical acid addition salts.

The pharmaceutical acid addition salts of the invention are typically formed by reacting the compound of Formula I with an equimolar or excess amount of acid. The reactants are generally combined in a mutual solvent such as diethylether, tetrahydrofuran, methanol, ethanol, isopropanol, benzene, and the like. The salts normally precipitate out of solution within about one hour to about ten days and can be isolated by filtration or other conventional methods.

Acids commonly employed to form acid addition salts are inorganic acids such as hydrochloric acid, hydrobromic acid, hydroiodic acid, sulfuric acid, phosphoric acid, and the like, and acids commonly employed to form such salts are inorganic acids such as hydrochloric acid, hydrobromic acid, hydroiodic acid, sulfuric acid, phosphoric acid, and the like, and organic acids, such as p-toluenesulfonic acid, methanesulfonic acid, oxalic acid, p-bromophenylsulfonic acid, carbonic acid, succinic acid, citric acid, benzoic acid, acetic acid and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, β-hydroxybutyrate, glycollate, tartrate, methanesulfonate, propanesulfonate, naphthalene-1-sulfonate, naphthalene-2-sulfonate, mandelate and the like.

The term "base addition salt" refers to a salt of a compound of Formula I prepared by reaction of a compound of Formula I with a mineral or organic base. For exemplification of pharmaceutical base addition salts see, e.g., Berge, S. M, Bighley, L. D., and Monkhouse, D. C., *J. Pharm. Sci.*, 66:1, 1977. The present invention also contemplates pharmaceutical base addition salts of compounds of Formula I. The skilled artisan would appreciate that some compounds of Formula I may be acidic in nature and accordingly react with any of a number of inorganic and organic bases to form pharmaceutical base addition salts. Examples of pharmaceutical base addition salts are the ammonium, lithium, potassium, sodium, calcium, magnesium, methylamino, diethylamino, ethylene diamino, cyclohexylamino, and ethanolamino salts, and the like of a compound of Formula I.

The compounds of Formula I, when existing as a diastereomeric mixture, may be separated into diastereomeric pairs of enantiomers by, for example, fractional crystallization from a suitable solvent, for example methanol or ethyl acetate or a mixture thereof. The pair of enantiomers thus obtained may be separated into individual stereoisomers by conventional means, for example by the use of an optically active acid as a resolving agent. Alternatively, any enantiomer of a compound of Formula I may be obtained by stereospecific synthesis using optically pure starting materials or reagents of known configuration or through enantioselective synthesis.

The compounds of Formula I can be prepared by one of ordinary skill in the art following a variety of procedures, some of which are illustrated in the procedures and schemes set forth below. The particular order of steps required to produce the compounds of Formula I is dependent upon the particular compound to being synthesized, the starting compound, and the relative liability of the substituted moieties. The reagents or starting materials are readily identifiable and available to one of skill in the art, and to the extent not commercially available, are readily synthesized by one of ordinary skill in the art following standard procedures commonly employed in the art, along with the various procedures and schemes set forth below.

The following Preparations and Examples are provided to better elucidate the practice of the present invention and should not be interpreted in any way as to limit the scope of the same. Those skilled in the art will recognize that various modifications may be made while not departing from the spirit and scope of the invention. All publications mentioned in the specification are indicative of the level of those skilled in the art to which this invention pertains.

The terms and abbreviations used in the instant Preparations and Examples have their normal meanings unless otherwise designated. For example, as used herein, the following terms have the meanings indicated: "eq" refers to equivalents; "N" refers to normal or normality, "M" refers to molar or molarity, "g" refers to gram or grams, "mg" refers to milligrams; "L" refers to liters; "mL" refers to milliliters; "µL" refers to microliters; "mol" refers to moles; "mmol" refers to millimoles; "psi" refers to pounds per square inch; "min" refers to minutes; "h" or "hr" refers to hours; "° C." refers to degrees Celsius; "TLC" refers to thin layer chromatography; "HPLC" refers to high performance liquid chromatography; "$R_f$" refers to retention factor; "$R_t$" refers to retention time; "δ" refers to part per million down-field from tetramethylsilane; "MS" refers to mass spectrometry, Observed Mass indicates (M+1) unless indicated otherwise. "MS(FD)" refers to field desorption mass spectrometry, "MS(IS)" refers to ion spray mass spectrometry, "MS(FIA)" refers to flow injection analysis mass spectrometry, "MS(FAB)" refers to fast atom bombardment mass spectrometry, "MS(EI)" refers to electron impact mass spectrometry, "MS(ES)" refers to electron spray mass spectrometry, "UV" refers to ultraviolet spectrometry, "$^1$H NMR" refers to proton nuclear magnetic resonance spectrometry. In addition, "IR" refers to infra red spectrometry, and the absorption maxima listed for the IR spectra are only those of interest and not all of the maxima observed. "RT" refers to room temperature.

General Preparations:

SCHEME A

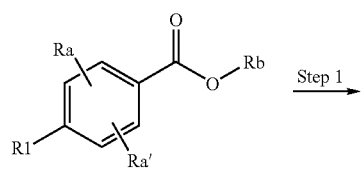

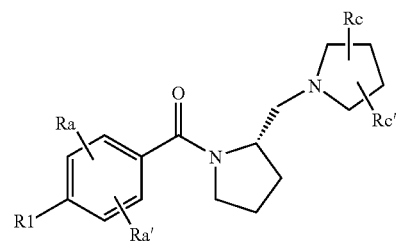

In Scheme A, $R_a$ and $R_{a'}$ are each independently but not limited to F, Cl, $CF_3$, alkyl and can include disubstituted compounds; $R_b$ is H, or the corresponding carboxylic acids salts; $R_c$ and $R_e$ are each independently but not limited to alkyl, amino, hydroxy, and R1 is, but not limited to a halogen, cyano, sulfone, nitro, acetyl, or an alkyl, branched alkyl group, cycloalkyl group which substituted with other functional groups not limited to sulfones, trifluoromethyl, halo, methoxy, ester, acid, phenyl etc. In Scheme A, Step 1 aryl carboxylic acids or the lithium, sodium or potassium salt of the acid where $R_b$ can be H, Li, Na or K are converted to the corresponding amides using a number of different methods known in the literature. Some of these methods can be found described in a review of coupling reagents in peptide synthesis by Klausner & Bodansky, Synthesis, 1972, 9, 453-463.

For example, 4-pentylbenzoic acid or the corresponding lithium or sodium salt is suspended a suitable organic solvent such as dichloromethane, DMF or mixtures thereof. A suitable amide coupling agent i.e EDC, DCC, TBTU, PS-carbodiimide etc., is added followed by HOBt, HATU, etc., at room temperature. Diisopropylethyl amine and suitable amine in this case, (S)(+)-1-(2-pyrrolidinylmethyl)pyrrolidine are added to the mixture. The mixture is stirred or shaken at room temperature for a period of 8-48 hours. The reaction is quenched by addition of water. The resulting mixture may be extracted, concentrated and purified according to techniques well known in the art.

Alternatively the corresponding acid chloride can be formed from the corresponding acid or salt thereof using thionyl chloride or oxalyl chloride and a few drops DMF, and treated with a suitable amine to give the desired amide. For example 4-bromo-2-fluorobenzoic acid and oxalyl chloride are combined in a suitable solvent such as dichloromethane, pyridine or mixtures thereof, and 2 drops of dimethylformamide are added as a catalyst. The reaction is stirred at room temperature for a period of 1-8 hours. After this time, the reaction is concentrated in vacuo. Total conversion to the acid chloride is assumed.

Alternatively the ether can be formed by a Mitsunobu or related reaction using an alkyl alcohol and a coupling agent such as DEAD, DIAD etc. with triphenyl phosphine in a suitable solvent such as THF or $CH_2Cl_2$. The reaction is quenched with water, and the resulting mixture may be extracted, concentrated, and purified according to techniques well known in the art.

Intermediate 1

4-(3-Oxo-3-phenyl-propenyl)-benzoic acid

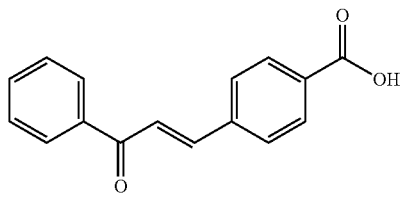

Sodium hydroxide (128.0 g, 3.2 mol) is dissolved in water (1400 mL) and ethanol (675 mL). The mixture is cooled to 20° C. and acetophenone (120 g, 0.5 mol) is added with mechanical stirring. 4-Carboxybenzaldehyde (75 g, 0.5 mol) and the reaction stirred at room temperature for 6 h. The reaction is acidified with concentrated HCl (300 mL) and extracted with ethyl acetate (3×). The combined organic portions are washed with water, saturated brine, dried, and evaporated in vacuo. The material is recrystallized from isopropanol with a small amount of methanol to obtain 48 g (38%) of the titled compound. m.p.=197-200° C.; Anal. Calcd for $C_{16}H_{12}O_3$: C, 76.18; H, 4.79. Found: C, 76.03; H, 5.05.

Intermediate 2

4-(3-Oxo-3-phenyl-propyl)-benzoic acid

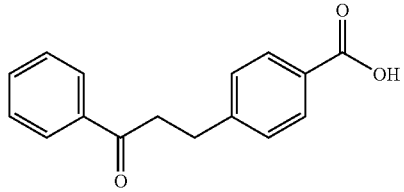

4-(3-Oxo-3-phenyl-propenyl)-benzoic acid (7.64 g, 30 mmol) is combined with Raney nickel (2 g) in ethanol (140 mL). The mixture is hydrogenated at room temperature and 50 psi for 1.5 h. The reaction is filtered evaporated in vacuo. The resulting residue is recrystallized from ethyl acetate to obtain 4.57 g (59%) of the titled compound. m.p.=145-147° C.; Anal. Calcd for $C_{16}H_{14}O_3$: C, 75.58; H, 5.55. Found: C, 75.60; H, 5.32.

Intermediate 3

4-(5-Oxo-5-phenyl-penta-1,3-dienyl)-benzoic acid

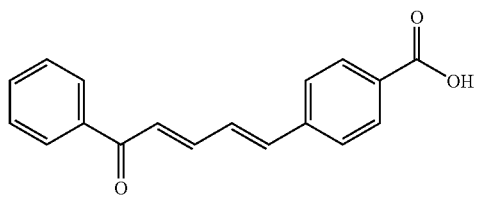

Sodium hydroxide (128.0 g, 3.2 mol) is dissolved in water (1400 mL) and ethanol (675 mL). Cinnamaldehyde (66.1 g, 0.5 mol) and 4-acetylbenzoic acid (82.1 g, 0.5 mol) are added and the mixture stirred for about 5 min. A thick precipitate is formed and the thick mixture is diluted with water (750 mL) and ethanol (750 mL). Stir at room temperature for 18 h. The reaction is cooled and acidified with concentrated HCl (270 mL). The mixture is extracted with ethyl acetate (3×). The combined organic portions are washed with water (2×), dried over $Na_2SO_4$, filtered and evaporated. The resulting solid is recrystallized from 2-methoxyethanol and washed with diethyl ether to obtain 36.1 g (26%) of yellow crystals. m.p.=210-214° C.; Anal. Calcd for $C_{18}H_{14}O_3$: C, 77.68; H, 5.07. Found: C, 77.47; H, 5.09.

Intermediate 4

4-(5-Phenyl-pentyl)-benzoic acid

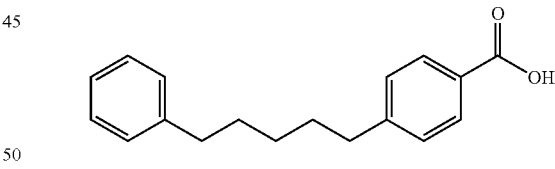

4-(5-Oxo-5-phenyl-penta-1,3-dienyl)-benzoic acid (13.9 g, 50 mmol) is dissolved in ethanol (280 mL). Concentrated $H_2SO_4$ (1 mL) and 5% palladium on carbon (2.8 g) are added and the mixture hydrogenated at 50° C. and 60 psi for 4 h. The reaction is filtered, diluted with water (1000 mL), and extracted several times with diethyl ether. The combined organic extracts are washed with 2 N NaOH. The aqueous portion is acidified with concentrated hydrochloric acid and extracted with diethyl ether. The ether extracts are washed with water, dried over $Na_2SO_4$, and evaporated to obtain a solid. The solid is recrystallized from hexanes to obtain 7.2 g (54%) of white crystals. m.p.=80-80.5° C.; Anal. Calcd for $C_{18}H_{20}O_2$: C, 80.56; H, 7.51. Found: C, 80.75; H, 7.34.

Intermediate 5

2-(R)-Methyl-1-(2-(S)-pyrrolidinylmethyl)pyrrolidine

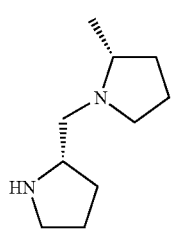

Equimolar amounts of (S) BOC proline (CAS 15761-39-4) and 2-(R)-methyl-pyrrolidine hydrochloride (CAS 135324-85-5) are coupled in a manner substantially analogous to Procedure D in dichloromethane to give 2(S)-(2(R)-methyl-pyrrolidine-1-carbonyl)-pyrrolidine-1-carboxylic acid tert-butyl ester. The material is deprotected by stirring in dichloromethane at 5-10° C. while trifluoroacetic acid (10 eq) is added and then stirred at room temperature for 18 h. The reaction is concentrated, dissolved in H$_2$O, and the pH is adjusted to 8-9 with K$_2$CO$_3$. The mixture is extracted several times with CH$_2$Cl$_2$. The extracts are combined, dried (Na$_2$SO$_4$), filtered, and concentrated in vacuo to give (2(R)-methyl-pyrrolidin-1-yl)-pyrrolidin-2-yl-methanone. A 1 M lithium aluminum hydride/THF solution (3 eq.) is diluted with an equal volume of THF and stirred under N$_2$ as a THF solution of (2(R)-methyl-pyrrolidin-1-yl)-pyrrolidin-2-yl-methanone is added dropwise, allowing the reaction to mildly exotherm. The reaction mixture is stirred at 40° C. for 45 min, and then at room temperature 18 h. The mixture is cooled in an ice bath and quenched with H$_2$O (3 eq.), 4 N NaOH (3 eq.), then H$_2$O (9 eq.) while keeping the reaction temperature less than 15° C. The mixture is stirred overnight, filtered, and the precipitate is washed three times with THF. The filtrate and washes are combined and concentrated to give 2-(R)-methyl-1-(2-(S)-pyrrolidinylmethyl)pyrrolidine. MS (ES+) 169.3 (M+H)$^+$. The title compound is used as such or is purified by SCX chromatography or distillation.

Intermediate 6

4-Bromo-2-fluorobenzoic acid chloride

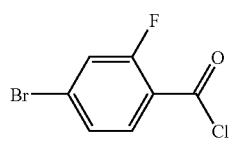

4-Bromo-2-fluorobenzoic acid (1.0 mmol) and oxalyl chloride (2.0 mmol) are combined in dichloromethane (0.10 M), and 2 drops of dimethylformamide are added as a catalyst. The reaction is stirred at room temperature for 3 h. After this time, the reaction is concentrated in vacuo. Total conversion to the acid chloride is assumed.

Intermediate 7

6-(4-Trifluoromethoxy-phenylsulfanyl)-nicotinic acid methyl ester

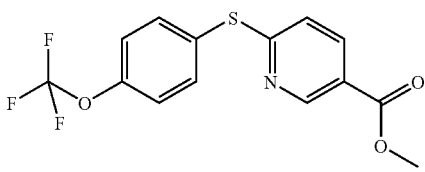

Procedure: To a stirring solution of methyl-6-chloronicotinate (200 mg, 1.17 mmol) and potassium carbonate (483 mg, 3.5 mmol) in N,N-dimethylformamide (6 mL), add 4-trifluoromethoxy-benzenethiol (340 mg, 1.75 mmol) and heat to 100° C. for two hours. After this time, remove the heat and wash the reaction with water while extracting with dichloromethane. Dry the organics with sodium sulfate, filter and concentrate in vacuo. Purify via radial chromatography eluting with ethyl acetate and hexane.

MS (m/e): 330.1 (M+1).

Intermediate 8

6-(4-Trifluoromethoxy-phenylsulfanyl)-nicotinic acid sodium salt

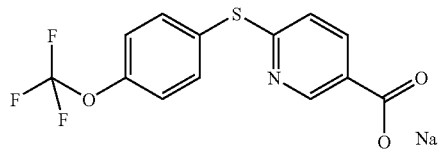

Procedure: To a stirring solution of 6-(4-trifluoromethoxy-phenylsulfanyl)-nicotinic acid methyl ester (See Intermediate 7) (52 mg, 0.158 mmol) in methanol/tetrahydrofuran (1:1) (0.15M), add 2N sodium hydroxide (0.08 mL, 0.161 mmol) and heat to reflux for one hour. After this time, remove the heat and concentrate in vacuo.

MS (m/e): 316.0 (M+1).

EXAMPLE 1

(S)-(4-Pentyl-phenyl)-(2-pyrrolidin-1-ylmethyl-pyrrolidin-1-yl)-methanone

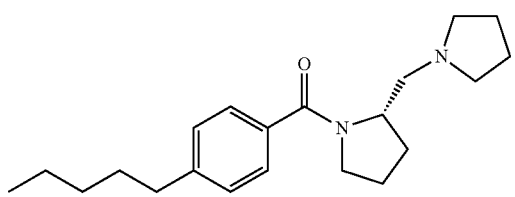

Procedure A: 4-Pentylbenzoic acid (62 mg, 0.32 mmol) and PS-carbodiimide (mmol/g=1.32, 484 mg, 0.64 mmol) are combined in 5.0 ml of 5% DMF in Dichloromethane and mixed well in a vial. (S)(+)-1-(2-Pyrrolidinylmethyl)pyrrolidine (50 mg) is added to this mixture and the vial is capped with a Teflon cap. The vial is shaken at room temperature overnight. The mixture is filtered and the resin is washed with dichloromethane. The filtrate is concentrated under $N_2$ gas and applied to silica-gel column chromatography ($CH_2Cl_2$ followed by $CH_2Cl_2$: 2M $NH_3$ in MeOH=45:1) to give the product. Observed mass: 329 (M+1).

EXAMPLE 2

(S)-(4-Methylsulfanyl-phenyl)-(2-pyrrolidin-1-ylmethyl-pyrrolidin-1-yl)-methanone

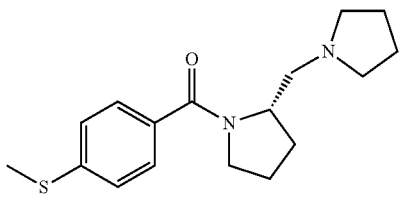

(S)-(4-Methylsulfanyl-phenyl)-(2-pyrrolidin-1-ylmethyl-pyrrolidin-1-yl)-methanone is prepared from 4-(methylthio)benzoic acid in a manner substantially similar Procedure A. Observed mass 305.

EXAMPLE 3

(S)-[4-(4-Methyl-cyclohexylsulfanyl)-phenyl]-(2-pyrrolidin-1-ylmethyl-pyrrolidin-1-yl)-methanone

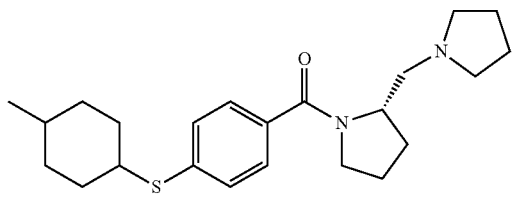

(S)-[4-(4-Methyl-cyclohexylsulfanyl)-phenyl]-(2-pyrrolidin-1-ylmethyl-pyrrolidin-1-yl)-methanone is prepared from 4-(4-methyl-cyclohexylsulfanyl)-benzoic acid in a manner substantially similar Procedure A. Observed mass 387.

EXAMPLE 4

(S)-(4-Methanesulfonyl-phenyl)-(2-pyrrolidin-1-ylmethyl-pyrrolidin-1-yl)-methanone

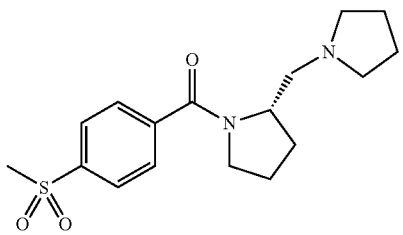

(S)-(4-Methanesulfonyl-phenyl)-(2-pyrrolidin-1-ylmethyl-pyrrolidin-1-yl)-methanone is prepared from 4-methanesulfonyl benzoic acid in a manner substantially similar Procedure A. Observed mass 337.

EXAMPLE 5

(S)-(2-Pyrrolidin-1-ylmethyl-pyrrolidin-1-yl)-p-tolyl-methanone

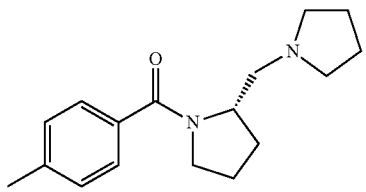

The title compound is prepared from p-toluic acid in a manner substantially similar Procedure A. Observed mass 273.

EXAMPLE 6

(S)-(4-Ethyl-phenyl)-(2-pyrrolidin-1-ylmethyl-pyrrolidin-1-yl)-methanone

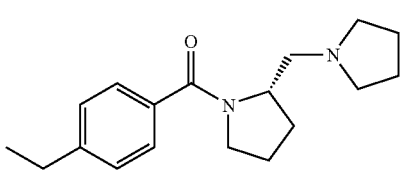

The title compound is prepared from 4-ethylbenzoic acid in a manner substantially similar Procedure A. Observed mass 287.

EXAMPLE 7

(S)-(4-Propyl-phenyl)-(2-pyrrolidin-1-ylmethyl-pyrrolidin-1-yl)-methanone

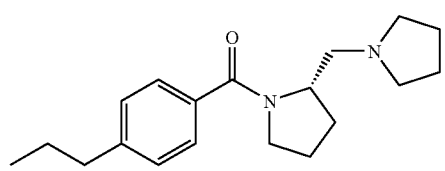

The title compound is prepared from 4-N-propylbenzoic acid in a manner substantially similar Procedure A. Observed mass 301.

EXAMPLE 8

(S)-(4-Butyl-phenyl)-(2-pyrrolidin-1-ylmethyl-pyrrolidin-1-yl)-methanone

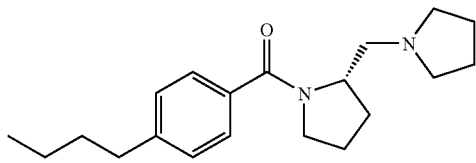

The title compound is prepared from 4-N-butylbenzoic acid in a manner substantially similar Procedure A. Observed mass 315.

EXAMPLE 9

(S)-(4-Benzyl-phenyl)-(2-pyrrolidin-1-ylmethyl-pyrrolidin-1-yl)-methanone

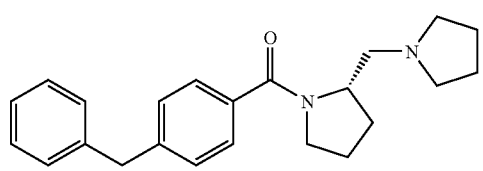

The title compound is prepared from diphenylmethane-4-carboxylic acid in a manner substantially similar Procedure A. Observed mass 349.

EXAMPLE 10

(S)-(3,4-Dimethyl-phenyl)-(2-pyrrolidin-1-ylmethyl-pyrrolidin-1-yl)-methanone

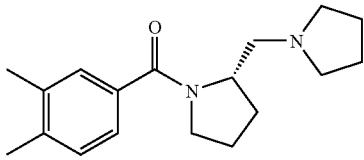

The title compound is prepared from 3,4-dimethylbenzoic acid in a manner substantially similar Procedure A. Observed mass 287.

EXAMPLE 11

(S)-(4-tert-Butyl-phenyl)-(2-pyrrolidin-1-ylmethyl-pyrrolidin-1-yl)-methanone

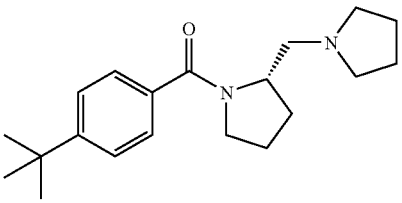

The title compound is prepared from 4-tert-butylbenzoic acid in a manner substantially similar Procedure A. Observed mass 315.

EXAMPLE 12

(S)-(4-Benzoyl-phenyl)-(2-pyrrolidin-1-ylmethyl-pyrrolidin-1-yl)-methanone

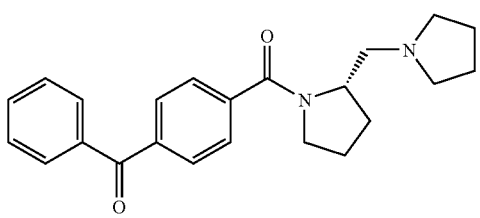

The title compound is prepared from 4-benzoylbenzoic acid in a manner substantially similar Procedure A. Observed mass 363.

EXAMPLE 13

(S)-(4-Cyclohexyl-phenyl)-(2-pyrrolidin-1-ylmethyl-pyrrolidin-1-yl)-methanone

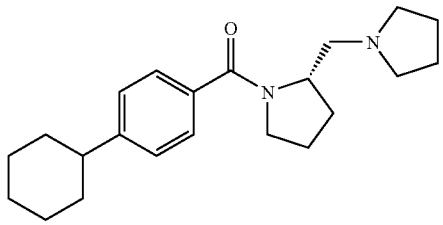

The title compound is prepared from 4-cyclohexylbenzoic acid in a manner substantially similar Procedure A. Observed mass 341.

EXAMPLE 14

1-Phenyl-3-[4-(2-(S)-pyrrolidin-1-ylmethyl-pyrrolidine-1-carbonyl)-phenyl]-propan-1-one

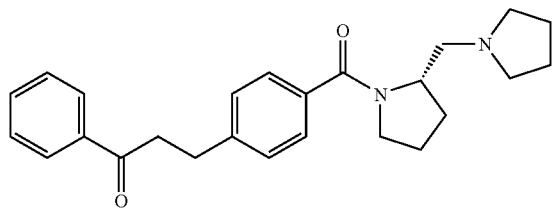

The title compound is prepared from 4-(3-oxo-3-phenyl-propyl)-benzoic acid (Intermediate 2), in a manner substantially similar Procedure A. Observed mass 391.

EXAMPLE 15

[4-(5-Phenyl-pentyl)-phenyl]-(2-(S)-pyrrolidin-1-ylmethyl-pyrrolidin-1-yl)-methanone

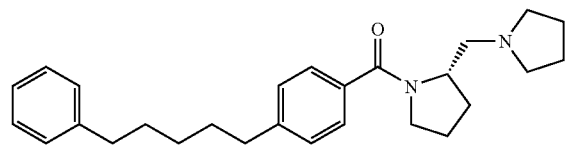

The title compound is prepared from 4-(5-phenyl-pentyl)-benzoic acid (Intermediate 4), in a manner substantially similar to Procedure A. Observed mass 405.

EXAMPLE 16

(S)-[4-(2-Chloro-ethyl)-phenyl]-(2-pyrrolidin-1-ylmethyl-pyrrolidin-1-yl)-methanone

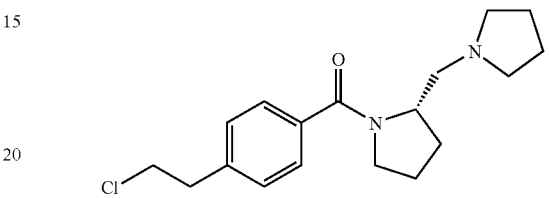

Add thionylchloride (6 mL) to 4-(2-chloroethyl)benzoic acid (1.00 g, 5.4 mmol) and stir at 50° C. for 30 min. Remove the excess thionylchloride in vacuo and dissolve the reside to dichloromethane (2 mL). Add this acid chloride solution to the mixture of triethylamine (656 mg, 6.5 mmol) and (S)(+)-1-(2-pyrrolidinylmethyl)pyrrolidine (1.00 g, 6.5 mmol) in dichloromethane (30 mL) at 0° C. and stir it at room temperature for 2 h. Dilute the reaction mixture and wash with brine, dry over sodium sulfate and remove the solvent. Purify the crude product by a silica-gel column chromatography (dichloromethane:2M ammonia in methanol=40:1) to give the title compound. 1.35 g (80%). Observed Mass 321.

EXAMPLE 17

(4-Bromo-2-fluoro-phenyl)-(2-(S)-pyrrolidin-1-ylmethyl-pyrrolidin-yl)methanone

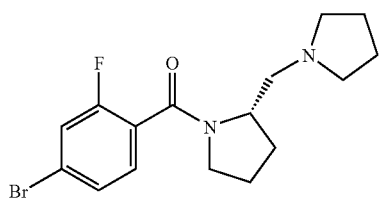

To a stirring solution of (S)-(+)-1-(2-pyrrolidinylmethyl)pyrrolidine (1.0 mmol) and N-methylmorpholine (1.0 mmol) in dichloromethane (0.10M), slowly add 4-Bromo-2-fluorobenzoic acid chloride (1.0 mmol) diluted in dichloromethane. Stir reaction at room temperature for one hour. After this time wash the reaction with saturated aqueous sodium bicarbonate while extracting with dichloromethane. Dry the organic layer with sodium sulfate, filter and concentrate in vacuo to give the title compound. MS (m/e): 355.1/357.1 (M+1).

EXAMPLE 18

(4-Fluoro-phenyl)-(2-(S)-pyrrolidin-1-ylmethyl-pyrrolidin-1-yl)-methanone

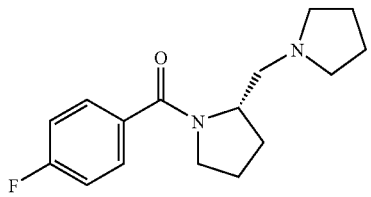

Procedure B: (S)(+)-1-(2-Pyrrolidinylmethyl)pyrrolidine (1.07 g, 6.93 mmol) and triethylamine (763 mg, 7.56 mmol) are dissolved in dichloromethane (20 mL) and cooled to 0° C. 4-Fluorobenzoyl chloride (1.00 g, 6.3 mmol) in dichloromethane (2.0 mL) is added to the mixture at 0° C. and stirred at room temperature for 3 h. The reaction mixture is washed with brine, dried over $Na_2SO_4$, filtered and evaporated. The residue is purified using silica-gel column chromatography ($CH_2Cl_2$:2M $NH_3$ in MeOH=40:1) to give 1.45 g (83%) of the title compound. Observed mass: 277 (M+1).

EXAMPLE 19

(4-Bromo-2-fluoro-phenyl)-[2-(S)-(2-(R)-methyl-pyrrolidin-1-ylmethyl)-pyrrolidin-1-yl]-methanone

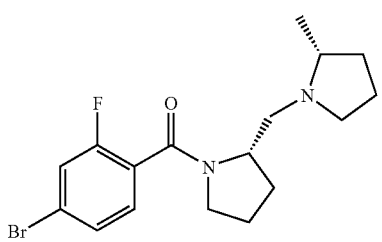

The title compound is prepared in a manner substantially analogous to Procedure C (see example 32) from 4-bromo-2-fluoro-benzoic acid (CAS 112704-79-7) and 2-(R)-Methyl-1-(2-(S)-pyrrolidinylmethyl)pyrrolidine. MS (FIA) 369/371 (MH+).

EXAMPLE 20

(S)-(2-Pyrrolidin-1-ylmethyl-pyrrolidin-1-yl)-(4-trifluoromethyl-phenyl)-methanone

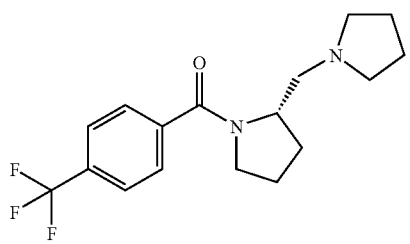

The title compound is prepared from 4-trifluoromethyl benzoic acid in a manner substantially similar to Procedure A. Observed mass 327.

EXAMPLE 21

(4-Bromo-phenyl)-(2-(S)-pyrrolidin-1-ylmethyl-pyrrolidin-yl)methanone

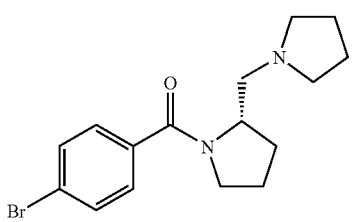

To a stirring solution of 4-bromobenzoic acid-2,5-dioxo-pyrrolidin-1-yl ester (3.5 g, 11.7 mmol), [which can be prepared from 4-bromobenzoic acid and N-hydroxy succinamide by the method of C. Mitsos, Chem Pharm Bull 48(2), 211-214 (2000), or purchased from Ambinter, CAS# 80586-82-9], in tetrahydrofuran (0.15 M), add (S)-(+)-1-(2-pyrrolidinylmethyl)pyrrolidine and heat to reflux for 4 h. After this time, remove the heat and wash the reaction with water while extracting with 10% isopropanol/dichloromethane. Dry the organic portion with sodium sulfate, filter and concentrate in vacuo. Purify the resulting residue on a silica column eluting with 2 M ammonia in methanol and dichloromethane to give (4-bromo-phenyl)-(2-(S)-pyrrolidin-1-ylmethyl-pyrrolidin-yl)methanone (93% yield with 80% purity). MS (m/e): 337.1 (M+1).

EXAMPLE 22

(S)-(4-Chloro-phenyl)-(2-(S)-pyrrolidin-1-ylmethyl-pyrrolidin-1-yl)-methanone

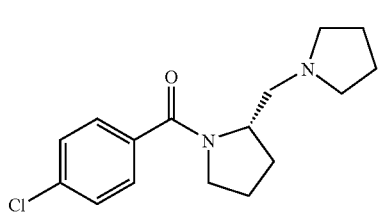

The title compound is prepared from 4-chlorobenzoic acid in a manner substantially similar to Procedure A. Observed mass 293.

EXAMPLE 23

4-(2-(S)-Pyrrolidin-1-ylmethyl-pyrrolidine-1-carbonyl)-benzonitrile

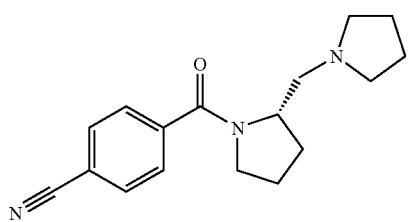

The title compound is prepared from 4-cyanobenzoic acid in a manner substantially similar to Procedure A. Observed mass 391.

EXAMPLE 24

(4-Nitro-phenyl)-(2-(S)-pyrrolidin-1-ylmethyl-pyrrolidin-1-yl)-methanone

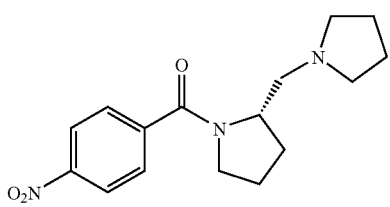

The title compound is prepared from 4-nitrobenzoic acid in a manner substantially similar to Procedure A. Observed mass: 304 (M+1).

EXAMPLE 25

(4-Bromo-2-trifluoromethyl-phenyl)-(2-(S)-pyrrolidin-1-ylmethyl-pyrrolidin-1-yl)-methanone

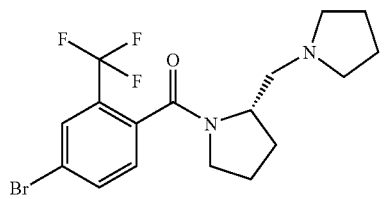

Procedure D: 4-Bromo-2-trifluoromethylbenzoic acid (CAS 320-31-0) (0.46 g, 1.7 mmol) is dissolved in dimethylformamide (5 ml) with stirring at room temperature. TBTU (0.558 g, 1.8 mmol), triethylamine (1 ml) and (S)(+)-1-(2-pyrrolidinylmethyl)pyrrolidine (0.26 g, 1.7 mmol) are added and this mixture is stirred at room temperature overnight. Water and ethyl acetate are added to the mixture. The aqueous layer is extracted several times with ethyl acetate. The combined organic layers are dried over MgSO$_4$ and evaporated. The crude product is purified by silica-gel column chromatography (gradient: 100% CH$_2$Cl$_2$ to 8% 2M NH$_3$ in MeOH/CH2Cl2) give the title compound. MS (FIA) 405/407 (MH+).

EXAMPLE 26

(4-Bromo-2,6-difluoro-phenyl)-(2-(S)-pyrrolidin-1-ylmethyl-pyrrolidin-1-yl)-methanone

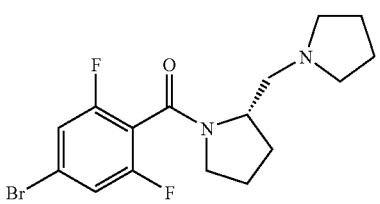

The title compound is prepared in a manner substantially analogous to Procedure D from 2,6-difluoro-4-bromobenzoic acid (CAS 183065-68-1). MS (HA) 405/407 (MH$^+$).

EXAMPLE 27

1-[4-(2-(S)-Pyrrolidin-1-ylmethyl-pyrrolidine-1-carbonyl)-phenyl]-ethanone hydrochloride salt

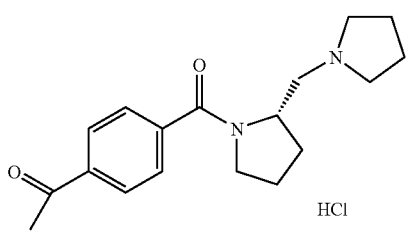

Procedure E: 4-Acetylbenzoic acid (Aldrich) (CAS# 586-89-0) (295 mg, 1.8 mmol) is suspended in dichloromethane (9 mL) and DMF (1 mL). EDC (344 mg, 1.8 mmol) and HOBt (243 mg, 1.8 mmol) are added at room temperature in that order. DIEA (0.63 mL, 3.6 mmol) and (S)(+)-1-(2-pyrrolidinylmethyl)pyrrolidine (185 mg, 1.2 mmol) are added to the mixture. The mixture is stirred at room temperature for overnight. Brine is added to the mixture. The aqueous layer is extracted with dichlormethane (2×), the combined organic layers are washed with aq. NaHCO$_3$, then brine (3×), dried over Na$_2$SO$_4$ and evaporated. The crude product is purified by an SCX column (MeOH wash, then elute with 2M NH$_3$ in MeOH). The product is then further purified by silica-gel column chromatography (gradient: 100% CH$_2$Cl$_2$ to 10% 2M NH$_3$ in MeOH/CH$_2$Cl$_2$) give the free base. The free base (312 mg, 1.04 mmol) is stirred in anhyd. MeOH (5 mL) and 1 N HCl/Et$_2$O (1.22 mL, 1.22 mmol) is added, stirred 10 minutes, evaporated, dissolved in anhyd. MeOH, evaporated, and the material is triturated in Et$_2$O, filtered, and dried in vacuo to the HCl salt as a white solid (350 mg, 87% yld). MS (ES+) 301.2 (free base).

EXAMPLE 28

(4-Cyclopropanecarbonyl-phenyl)-(2-(S)-pyrrolidin-1-ylmethyl-pyrrolidin-1-yl)-methanone hydrochloride salt

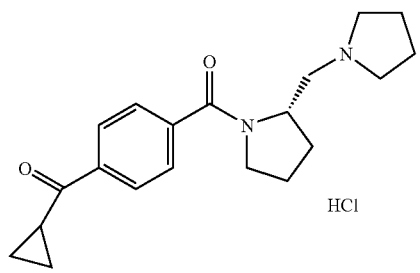

The title compound is prepared in a manner substantially analogous to Procedure E starting from 4-cyclopropanecarbonyl-benzoic acid (CAS# 303021-37-6; Dorwald, F et al. WO 2000063208) and (S)(+)-1-(2-pyrrolidinylmethyl)pyrrolidine MS (ES+) 327.2 (M+H)$^+$.

EXAMPLE 29

(2-(S)-Pyrrolidin-1-ylmethyl-pyrrolidin-1-yl)-[6-(4-trifluoromethoxy-phenylsulfanyl)-pyridin-3-yl]-methanone dihydrochloride salt

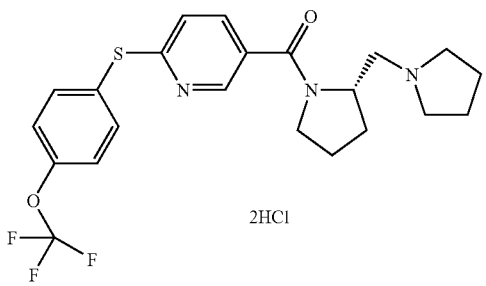

To a stirring solution of 6-(4-trifluoromethoxy-phenylsulfanyl)-nicotinic acid sodium salt (54 mg, 0.158 mmol) (see Intermediate 8) and n-methyl morpholine (0.02 mL, 0.158 mmol) in dichloromethane (2.0 mL) in a 0° C. ice bath, add 2-chloro-4,6-dimethoxy-1,3,5-triazine (28 mg, 0.158 mmol). Remove the ice bath and stir for 45 minutes. After this time, add (S)-(+)-1-(2-pyrrolidinylmethyl)pyrrolidine (24 mg, 0.158 mmol) and stir at room temperature for 2 hours. After this time, wash the reaction with saturated aqueous sodium bicarbonate while extracting with 10% isopropanol/dichloromethane. Dry the organic layer with sodium sulfate, filter and concentrate in vacuo. Purify via chromatography eluting with 2M ammonia in methanol and dichloromethane. Dissolve the purified free base in minimal dichloromethane and add 1M HCl in ether in slight excess followed by hexane. Concentrate in vacuo to give the titled compound. MS (m/e): 452.2 (M+1).

EXAMPLE 30

(4-Benzenesulfonyl-phenyl)-(2-(S)-pyrrolidin-1-ylmethyl-pyrrolidin-1-yl)-methanone

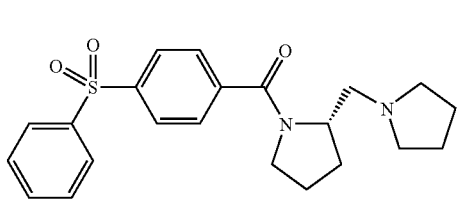

The title compound is prepared in a manner substantially analogous to the procedures found in Intermediate 6 and Example 17 using 4-(phenylsulfonyl)-benzoic acid [CAS# 5361-54-6] and (S)-(+)-1-(2-pyrrolidinylmethyl)pyrrolidine. MS (m/e): 399.2 (M+1).

EXAMPLE 31

(5-Benzylsulfanyl-pyridin-2-yl)-(2-(S)-pyrrolidin-1-ylmethyl-pyrrolidin-1-yl)-methanone: is-trifluoroacetic acid salt

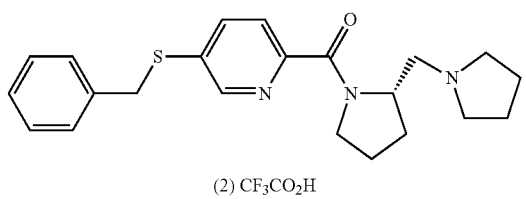

To a stirring solution of 5-Benzylsulfanyl-pyridine-2-carboxylic acid (0.045 g, 0.183 mmol) (which can be prepared from Butyl 6-methyl-3-pyridyl sulfoxide by the method of N. Finch, J. Med Chem., 21(12), 1269-1274, 1978.) in DMF (2 ml), add EDC (0.036 g, 0.188 mmol), (S)(+)-1-(2-Pyrrolidinylmethyl)pyrrolidine (0.028 g, 0.183 mmol) and the mixture is stirred at room temperature for 15 hours. The mixture is diluted with ethyl acetate and washed successively with a saturated sodium bicarbonate solution and brine. The organic layers are separated, dried with anhydrous sodium sulfate, filtered, and concentrated to a crude residue. The residue is purified by well known reverse phase techniques using TFA/water as the mobile phase. The desired fractions are concentrated to give pure titled compound. MS (m/e): 382.2 M+1 (free base).

EXAMPLE 32

(2-(S)-Pyrrolidin-1-ylmethyl-pyrrolidin-1-yl)-(-4-bromo-3-fluoro-phenyl-4-yl)-methanone

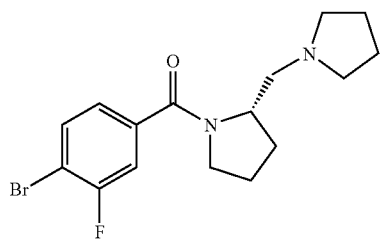

Procedure C: 4-Bromo-3-fluorobenzoic acid (CAS 153556-42-4) (0.5 g, 2.28 mmol) is dissolved in dichloromethane (25 ml) containing dimethylformamide (200 µl) with stirring at room temperature. Oxalyl chloride (0.5 ml, 5.7 mmol) is added and the reaction is left to stir overnight. The solvent is removed under reduced pressure and the residue is taken up in dichloromethane (15 ml) and added dropwise to a solution of triethylamine (1 ml) and (S)(+)-1-(2-pyrrolidinylmethyl)pyrrolidine (0.36 g, 2.3 mmol) and this mixture is stirred at room temperature for two hours. Aqueous sodium hydroxide solution is added to the mixture and the organic layer is collected, dried over MgSO$_4$ and evaporated to give the product. MS (FIA) 354/356 (MH$^+$).

EXAMPLE 33

(4-Bromo-phenyl)-[2-(S)-(2-(R)-Methyl-pyrrolidin-1-ylmethyl)-pyrrolidin-1-yl]-methanone

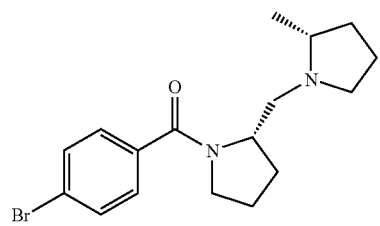

The title compound is prepared in a manner substantially analogous to Procedure C using commercially available 4-bromo benzoic acid, 2-(R)-methyl-1-(2-(S)-pyrrolidinylmethyl)pyrrolidine, and thionyl chloride in place of oxalyl chloride. (MS (ES+) 352.3 (M+H)$^+$

EXAMPLE 34

(4-Bromo-2,6-difluoro-phenyl)-(2-(R)-methyl-1-(2-(S)-pyrrolidinylmethyl)pyrrolidin-1-yl)-methanone

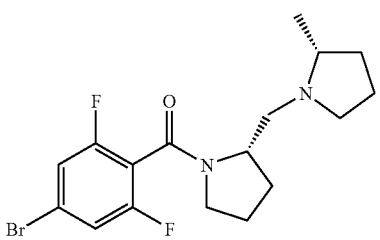

The title compound is prepared in a manner substantially analogous to Procedure D from 2,6-difluoro-4-bromobenzoic acid (CAS 183065-68-1) and 2-(R)-Methyl-1-(2-(S)-pyrrolidinylmethyl)pyrrolidine. MS (FIA) 387/389 (MH$^+$).

Further embodiments of the invention include the compounds of formulae X1 to X34. A further embodiment of the invention are any novel intermediate preparations described herein which are useful for preparing the histamine H3 receptor antagonists or inverse agonists of formulae I, or X1 to X34.

TABLE 1

| Formula Number | Structure |
|---|---|
| X1 | 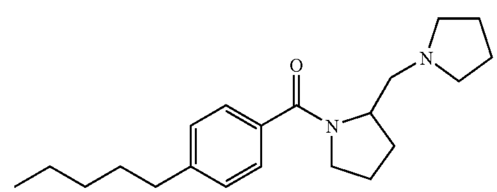 |
| X2 | 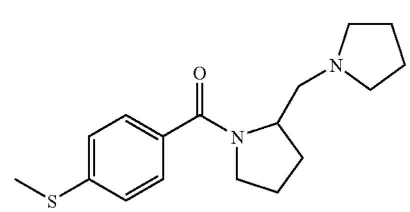 |
| X3 | 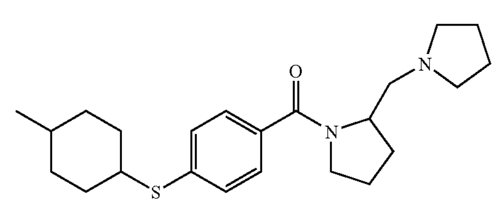 |

TABLE 1-continued
| Formula Number | Structure |
|---|---|
| X4 | 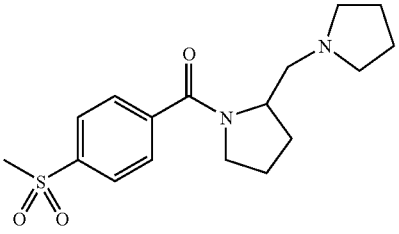 |
| X5 | 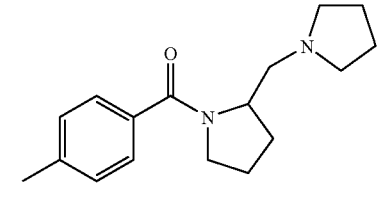 |
| X6 | 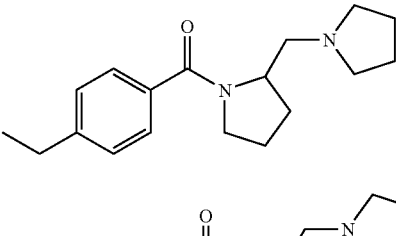 |
| X7 | 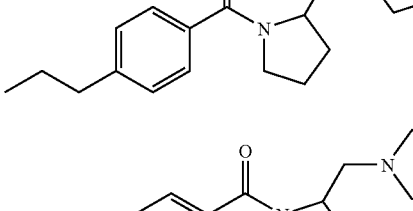 |
| X8 | 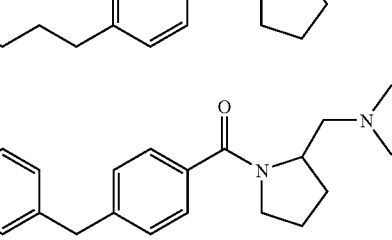 |
| X9 | 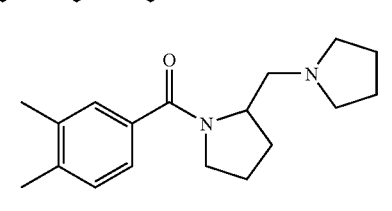 |
| X10 | 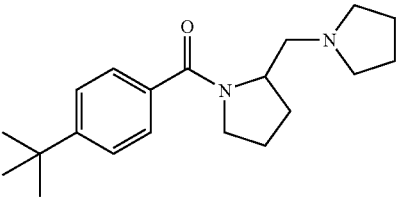 |
| X11 | 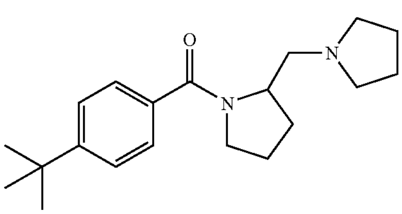 |
| X12 | 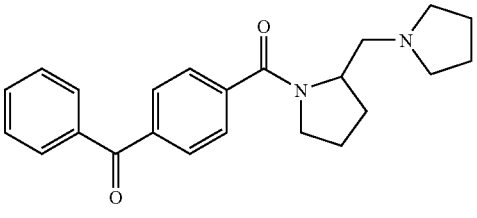 |
| X13 | 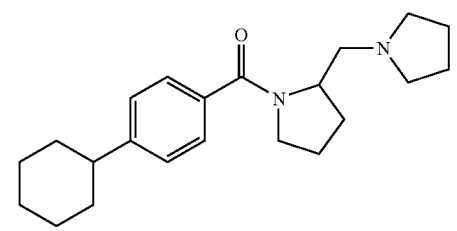 |
| X14 | 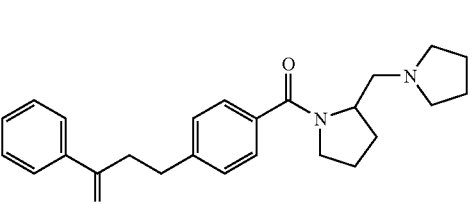 |
| X15 | 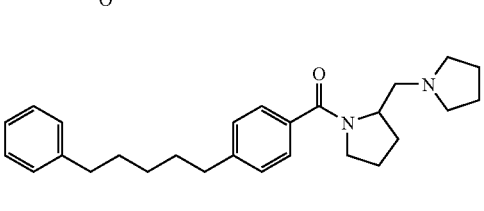 |
| X16 | 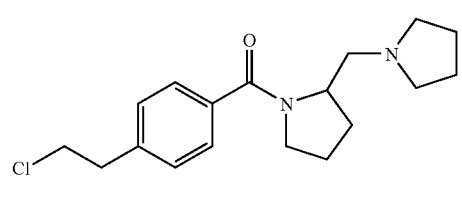 |
| X17 | 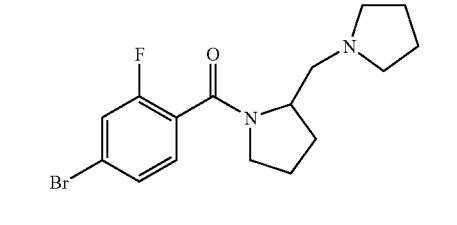 |
| X18 | 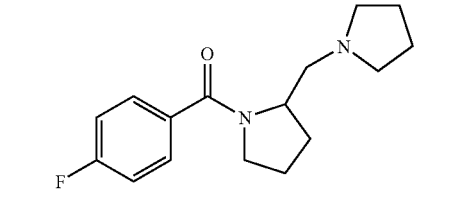 |

TABLE 1-continued

| Formula Number | Structure |
|---|---|
| X19 | 2-methyl-1-{[(4-bromo-2-fluorophenyl)carbonyl]pyrrolidin-2-yl}methyl)pyrrolidine |
| X20 | {4-(trifluoromethyl)phenyl}carbonyl-2-(pyrrolidin-1-ylmethyl)pyrrolidine |
| X21 | (4-bromophenyl)carbonyl-2-(pyrrolidin-1-ylmethyl)pyrrolidine |
| X22 | (4-chlorophenyl)carbonyl-2-(pyrrolidin-1-ylmethyl)pyrrolidine |
| X23 | 4-cyanophenyl carbonyl-2-(pyrrolidin-1-ylmethyl)pyrrolidine |
| X24 | (4-nitrophenyl)carbonyl-2-(pyrrolidin-1-ylmethyl)pyrrolidine |
| X25 | (4-bromo-2-(trifluoromethyl)phenyl)carbonyl-2-(pyrrolidin-1-ylmethyl)pyrrolidine |
| X26 | (4-bromo-2,6-difluorophenyl)carbonyl-2-(pyrrolidin-1-ylmethyl)pyrrolidine |
| X27 | (4-acetylphenyl)carbonyl-2-(pyrrolidin-1-ylmethyl)pyrrolidine |
| X28 | (4-(cyclopropylcarbonyl)phenyl)carbonyl-2-(pyrrolidin-1-ylmethyl)pyrrolidine |
| X29 | {6-[4-(trifluoromethoxy)phenylthio]pyridin-3-yl}carbonyl-2-(pyrrolidin-1-ylmethyl)pyrrolidine |
| X30 | {4-(phenylsulfonyl)phenyl}carbonyl-2-(pyrrolidin-1-ylmethyl)pyrrolidine |
| X31 | {5-(benzylthio)pyridin-2-yl}carbonyl-2-(pyrrolidin-1-ylmethyl)pyrrolidine |
| X32 | (4-bromo-3-fluorophenyl)carbonyl-2-(pyrrolidin-1-ylmethyl)pyrrolidine |

TABLE 1-continued

| Formula Number | Structure |
|---|---|
| X33 | (4-bromophenyl)(2-((2-methylpyrrolidin-1-yl)methyl)pyrrolidin-1-yl)methanone |
| X34 | (4-bromo-2,6-difluorophenyl)(2-((2-methylpyrrolidin-1-yl)methyl)pyrrolidin-1-yl)methanone |

The pharmaceutical salts of the invention are typically formed by reacting a compound of Formula I with an equimolar or excess amount of acid or base. The reactants are generally combined in a mutual solvent such as diethylether, tetrahydrofuran, methanol, ethanol, isopropanol, benzene, and the like for acid addition salts, or water, an alcohol or a chlorinated solvent such as dichloromethane for base addition salts. The salts normally precipitate out of solution within about one hour to about ten days and can be isolated by filtration or other conventional methods.

Acids commonly employed to form pharmaceutical acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, ethanesulfonic acid, oxalic acid, p-bromophenylsulfonic acid, carbonic acid, succinic acid, citric acid, tartaric acid, benzoic acid, acetic acid, and the like. Preferred pharmaceutical acid addition salts are those formed with mineral acids such as hydrochloric acid, hydrobromic acid, and sulfuric acid, and those formed with organic acids such as maleic acid, tartaric acid, and methanesulfonic acid.

Bases commonly employed to form pharmaceutical base addition salts are inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

The optimal time for performing the reactions of the Schemes, Preparations, and Procedures can be determined by monitoring the progress of the reaction via conventional chromatographic techniques. Furthermore, it is preferred to conduct the reactions of the invention under an inert atmosphere, such as, for example, argon, or, particularly, nitrogen. Choice of solvent is generally not critical so long as the solvent employed is inert to the ongoing reaction and sufficiently solubilizes the reactants to effect the desired reaction. The compounds are preferably isolated and purified before their use in subsequent reactions. Some compounds may crystallize out of the reaction solution during their formation and then collected by filtration, or the reaction solvent may be removed by extraction, evaporation, or decantation. The intermediates and final products of Formula I may be further purified, if desired by common techniques such as recrystallization or chromatography over solid supports such as silica gel or alumina.

The skilled artisan will appreciate that not all substituents are compatible with all reaction conditions. These compounds may be protected or modified at a convenient point in the synthesis by methods well known in the art.

The compound of Formula I is preferably formulated in a unit dosage form prior to administration. Therefore, yet another embodiment of the present invention is a pharmaceutical composition comprising a compound of Formula I and one or more pharmaceutically acceptable carriers, diluents or excipients, and can be administered by a variety of routes. Such pharmaceutical compositions and processes for preparing same are well known in the art. See, e.g. REMINGTON: THE SCIENCE AND PRACTICE OF PHARMACY (A. Gennaro, et al., eds., 19$^{th}$ ed., Mack Publishing Co., 1995).

Preferably the compound is administered orally. Preferably, the pharmaceutical preparation is in a unit dosage form. In such form, the preparation is subdivided into suitably sized unit doses containing appropriate quantities of the active components, e.g., an effective amount to achieve the desired purpose.

The quantity of the inventive active composition in a unit dose of preparation may be generally varied or adjusted from about 0.01 milligrams to about 1,000 milligrams, preferably from about 0.01 to about 950 milligrams, more preferably from about 0.01 to about 500 milligrams, and typically from about 1 to about 250 milligrams, according to the particular application. The actual dosage employed may be varied depending upon the patient's age, sex, weight and severity of the condition being treated. Such techniques are well known to those skilled in the art. Generally, the human oral dosage form containing the active ingredients can be administered 1 or 2 times per day.

Compounds of Formula I are effective as antagonists or inverse agonists of the histamine H3 receptor, and thus inhibit the activity of the H3 receptor. More particularly, these compounds are selective antagonists or inverse agonists of the histamine H3 receptor. As selective antagonists or inverse agonists, the compounds of Formula I are useful in the treatment of diseases, disorders, or conditions responsive to the inactivation of the histamine H3 receptor, including but not limited to obesity and other eating-related disorders, and cognitive disorders. Selective antagonists or inverse agonists of H3R are understood to raise brain histamine levels, and possibly that of other monoamines, resulting in inhibition of food consumption while minimizing peripheral consequences. Although a number of H3R antagonists are known in the art, none have proven to be satisfactory obesity or cognitive drugs. There is increasing evidence that histamine plays an important role in energy homeostasis. Histamine, acting as a neurotransmitter in the hypothalamus, suppressed appetite. Histamine is an almost ubiquitous amine found in many cell types and it binds to a family of G protein-coupled receptors (GPCRs). This family provides a mechanism by which histamine can elicit distinct cellular responses based on receptor distribution. Both the H1R and H2R are widely distributed. H3R is primarily expressed in the brain, notably in the thalamus and caudate nucleus. High density of expression of H3R was found in feeding center of the brain. A novel histamine receptor GPRv53 has been recently identified. GPRv53 is found in high levels in peripheral white blood cells; only low levels have been identified in the brain by some investigators while others cannot detect it in the brain. However, any drug discovery effort initiated around H3R must consider GPRv53 as well as the other subtypes.

The compounds of the present invention can readily be evaluated by using a competitive inhibition Scintillation Proximity Assay (SPA) based on a H3R binding assay using [3H] α methylhistamine as ligand. Stable cell lines, including but not limited to HEK can be transfected with cDNA coding for H3R to prepare membranes used for the binding assay. The technique is illustrated below (Preparation of Histamine Receptor Subtype Membranes) for the histamine receptor subtypes.

Membranes isolated as described in (Preparation of Histamine Receptor Subtype Membranes) are used in a [35S] GTPχS functional assay. Binding of [35S]GTPχS to membranes indicates agonist activity. Compounds of the invention of Formula I or Formula II are tested for their ability to inhibit binding in the presence of agonists. Alternately, the same transfected cell lines are used for a cAMP assay wherein H3R agonists inhibit forskolin-activated synthesis of cAMP. Compounds of Formula I or Formula II are tested for their ability to permit forskolin-stimulated cAMP synthesis in the presence of agonist.

Preparation of Histamine Receptor Subtype Membranes

A. Preparation H1R Membranes cDNA for the human histamine 1 receptor (H1R) is cloned into a mammalian expression vector containing the CMV promoter (pcDNA3.1(+), Invitogen) and transfected into HEK293 cells using the FuGENE Tranfection Reagent (Roche Diagnostics Corporation). Transfected cells are selected using G418 (500 μ/ml). Colonies that survived selection are grown and tested for histamine binding to cells grown in 96-well dishes using a scintillation proximity assay (SPA) based radioligand binding assay. Briefly, cells, representing individual selected clones, are grown as confluent monolayers in 96-well dishes (Costar Clear Bottom Plates, #3632) by seeding wells with 25,000 cells and growing for 48 hours (37° C., 5% $CO_2$). Growth media is removed and wells are rinsed two times with PBS (minus $Ca^{2+}$ or $Mg^{2+}$). For total binding, cells are assayed in a SPA reaction containing 50 mM Tris-HCL (assay buffer), pH 7.6, 1 mg wheat germ agglutinin SPA beads (Amersham Pharmacia Biotech, #RPNQ0001), and 0.8 nM $^3$H-pyrilamine (Net-594, NEN) (total volume per well=200 μl). Astemizole (10 μM, Sigma #A6424) is added to appropriate wells to determine non-specific binding. Plates are covered with FasCal and incubated at room temperature for 120 minutes. Following incubation, plates are centrifuged at 1,000 rpm (~800 g) for 10 minutes at room temperature. Plates are counted in a Wallac Trilux 1450 Microbeta scintillation counter. Several clones are selected as positive for binding, and a single clone (H1R40) is used to prepare membranes for binding studies. Cell pellets, representing ~10 grams, are resuspended in 30 ml assay buffer, mixed by vortexing, and centrifuged (40,000 g at 4° C.) for 10 minutes. The pellet resuspension, vortexing, and centrifugation is repeated 2 more times. The final cell pellet is resuspended in 30 ml and homogenized with a Polytron Tissue Homogenizer. Protein determinations are done using the Coomassie Plus Protein Assay Reagent (Pierce). Five micrograms of protein is used per well in the SPA receptor-binding assay.

B. Preparation H2R Membranes cDNA for the human histamine 2 receptor is cloned, expressed and transfected into HEK 293 cells as described above. Histamine binding to cells is assayed by SPA described above. For total binding, cells are assayed in a SPA reaction containing 50 mM Tris-HCl (assay buffer), pH 7.6, 1 mg wheat germ agglutinin SPA beads (Amersham Pharmacia Biotech, #RPNQ0001), and 6.2 nM $^3$H-tiotidine (Net-688, NEN) (total volume per well=200 μl). Cimetidine (10 μM, Sigma #C4522) is added to appropriate wells to determine non-specific binding.

Several clones are selected as positive for binding, and a single clone (H2R10) is used to prepare membranes for binding studies. Five micrograms of protein is used per well in the SPA receptor-binding assay.

C. Preparation of H3R Membranes cDNA for the human histamine 3 receptor is cloned and expressed as described in (A. Preparation H1R membranes), above. Transfected cells are selected using G418 (500 μ/ml), grown, and tested for histamine binding by the SPA described above. For total binding, cells are assayed in a SPA reaction described above containing 50 mM Tris-HCL (assay buffer), pH 7.6, 1 mg wheat germ agglutinin SPA beads (Amersham Pharmacia Biotech, #RPNQ0001), and 1 nM (3H)-n-alpha-methylhistamine (NEN, NET1027) (total volume per well=200 μl). Thioperimide is added to determine non-specific binding. Several clones are selected as positive for binding, and a single clone (H3R8) is used to prepare membranes for binding studies described above. Five micrograms of protein is used per well in the SPA receptor-binding assay.

All compounds set forth in the examples exhibit affinity for the H3 receptor greater than 1 uM. Preferred compounds of the invention exhibit affinity for the H3 receptor greater than 200 nM. Most preferred compounds of the invention exhibit affinity for the H3 receptor greater than 20 nM.

D. Preparation of GPRv53 Membranes cDNA for the human GPRv53 receptor is cloned and expressed as described in (A. Preparation H1R membranes), above. Transfected cells are selected, tested for histamine binding, and selected. HEK293 GPRv53 50 cells are grown to confluency in DMEM/F12 (Gibco) supplemented with 5 FBS and 500 ug/ml G418 and washed with Delbecco's PBS (Gibco) and harvested by scraping. Whole cells are homogenized with a Polytron tissuemizer in binding buffer, 50 mM Tris pH 7.5. Cell lysates, 50 ug, are incubated in 96 well dishes with 3 nM (3H) Histamine and compounds in binding buffer for 2 hours at room temperature. Lysates are filtered through glass fiber filters (Perkin Elmer) with a Tomtec cell harverster. Filters are counted with melt-on scintillator sheets (Perkin Elmer) in a Wallac Trilux 1450 Microbeta Scintillation counter for 5 minutes.

Pharmacological Results cAMP ELISA

HEK293 H3R8 cells prepared as described above are seeded at a density of 50,000 cells/well and grown overnight in DMEM/F12 (Gibco) supplemented with 5% FBS and 500 ug/ml G418. The next day tissue culture medium is removed and replaced with 50 μl cell culture medium containing 4 mM 3-isobutyl-1-methylxanthine (Sigma) and incubated for 20 minutes at room temperature. Antagonist are added in 50 μl cell culture medium and incubated for 20 minutes at room temperature. Agonist R (−)α methylhistamine (RBI) at a dose response from $1\times10^{-10}$ to $1\times10^{-5}$ M is then added to the wells in 50 μl cell culture medium and incubated for 5 minutes at room temperature. Then 50 μl of cell culture medium containing 20 μM Forskolin (Sigma) is added to each well and incubated for 20 minutes at room temperature. Tissue culture medium is removed and cells are lysed in 0.1M HCl and cAMP is measured by ELISA (Assay Designs, Inc.).

[35S] GTP γ [S] Binding Assay

Antagonist activity of selected compounds is tested for inhibition of [35S] GTP γ [S] binding to H3R membranes in the presence of agonists. Assays are run at room temperature in 20 mM HEPES, 100 mM NaCl, 5 mM $MgCl_2$ and 10 uM GDP at pH 7.4 in a final volume of 200 ul in 96-well Costar plates. Membranes isolated from H3R8-expressing HEK293 cell line (20 ug/well) and GDP are added to each well in a volume of 50 μl assay buffer. Antagonist is then added to the wells in a volume of 50 μl assay buffer and incubated for 15 minutes at room temperature. Agonist R(−)alpha methylhistamine (RBI) at either a dose response from $1\times10^{-10}$ to $1\times10^{-5}$ M or fixed concentration of 100 nM are then added to the wells in a volume of 50 μl assay buffer and incubated for 5 minutes at room temperature. GTP γ [$^{35}$S] is added to each well in a volume of 50 μl assay buffer at a final concentration of 200 μM, followed by the addition of 50 μl of 20 mg/ml WGA coated SPA beads (Amersham). Plates are counted in Wallac Trilux 1450 Microbeta scintillation counter for 1 minute. Compounds that inhibit more than 50% of the specific binding of radioactive ligand to the receptor are serially diluted to determine a K[i] (nM). The results are given below for the indicated compound.

TABLE 2

| Example | Ki (nM) |
|---|---|
| 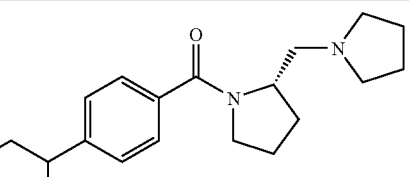 | 47 |
| 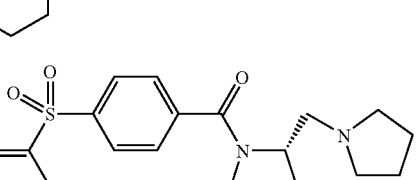 | 12 |

From the above description, one skilled in the art can ascertain the essential characteristics of the present invention, and without departing from the spirit and scope thereof, can make various changes and modifications of the invention to adapt it to various usages and conditions. Thus, other embodiments are also within the claims.

What is claimed is:
1. A compound structurally represented by Formula I

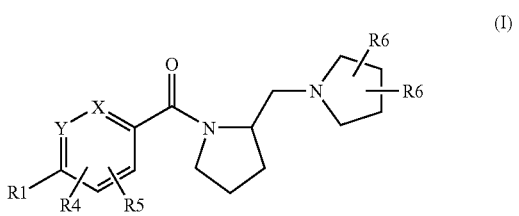

(I)

or a pharmaceutically acceptable salt thereof, wherein:
Y independently represents carbon;
X independently represents carbon or nitrogen;
R1 is independently
—CN, —NO$_2$, —(C$_1$-C$_7$) alkyl(optionally substituted with 1 to 3 halogens), —(C$_3$-C$_8$) cycloalkyl, —(C$_1$-C$_7$) alkyl-S(O)$_2$—(C$_1$-C$_3$) alkyl, —(C$_1$-C$_7$) alkyl-C(O)—O—R3, —(C$_1$-C$_7$) alkyl-S(O)$_2$-phenyl substituted three times with R2, —(C$_1$-C$_7$) alkyl-S—(C$_1$-C$_7$) alkyl, —(C$_1$-C$_7$) alkyl-(C$_3$-C$_8$) cycloalkyl, —(C$_1$-C$_7$) alkyl-phenyl substituted three times with R2, —C(O)-phenyl substituted three times with R2, —C(O)—(C$_1$-C$_7$) alkyl, —C(O)—(C$_3$-C$_8$) cycloalkyl, —(C$_1$-C$_7$) alkyl-C(O)-phenyl substituted three times with R2, —S—(C$_1$-C$_7$) alkyl, —S—(C$_1$-C$_7$) alkyl-phenyl substituted three times with R2, —S—(C$_3$-C$_8$) cycloalkyl-(C$_1$-C$_7$) alkyl, —S—(C$_3$-C$_8$) cycloalkyl, —S—(C$_2$-C$_7$) alkenyl, —S-phenyl substituted three times with R2, —SO$_2$-phenyl substituted three times with R2, —SO$_2$R7, —S(O)R7, —(C$_2$-C$_7$) alkenyl, —(C$_3$-C$_8$) cycloalkenyl, —(C$_2$-C$_7$) alkenyl-S (O)$_2$—(C$_1$-C$_3$) alkyl, —(C$_2$-C$_7$) alkenyl-C(O)—O—R3, —(C$_2$-C$_7$) alkenyl-S(O)$_2$-phenyl substituted three times with R2, —(C$_2$-C$_7$) alkenyl-S—(C$_1$-C$_7$) alkyl, —(C$_2$-C$_7$) alkenyl-(C$_3$-C$_8$) cycloalkyl, or —(C$_2$-C$_7$) alkenyl-phenyl substituted three times with R2;
R2 is independently at each occurrence
—H, -halogen, —(C$_1$-C$_7$) alkyl(optionally substituted with 1 to 3 halogens), —C(O)R7, —C(O)OR7, —C(O)(C$_3$-C$_8$)cycloalkyl, —OCF$_3$, —OR7, —SR7, —SO$_2$R7, —SO$_2$CF$_3$, or —S(O)R7;
R3 is independently at each occurrence
—H, or —(C$_1$-C$_3$) alkyl(optionally substituted with 1 to 3 halogens);
R4 and R5 are independently at each occurrence
—H, —(C$_1$-C$_3$) alkyl(optionally substituted with 1 to 3 halogens), or —OR3, provided that when X is nitrogen, then R4 or R5 are not attached to X;
R6 is independently at each occurrence
—H, -halogen, —CF$_3$, —(C$_1$-C$_3$) alkyl(optionally substituted with 1 to 3 halogens), or —OR3; and
R7 is independently at each occurrence
—H, —(C$_1$-C$_7$) alkyl(optionally substituted with 1 to 3 halogens), or —(C$_2$-C$_7$) alkenyl.
2. The compound or salt of claim 1 wherein X is carbon.
3. The compound or salt of claim 1 wherein X is nitrogen.
4. The compound or salt of claim 2 wherein R1 is —CN, —NO$_2$, —(C$_1$-C7) alkyl, —(C$_3$-C$_8$) cycloalkyl, —(C$_1$-C$_7$) alkyl-S(O)$_2$—(C$_1$-C$_3$) alkyl, —(C$_1$-C$_7$) alkyl-C(O)—O—R3, —(C$_1$-C$_7$) alkyl-S(O)$_2$-phenyl substituted three times with R2, —(C$_1$-C$_7$) alkyl-S—(C$_1$-C$_7$) alkyl, —(C$_1$-C$_7$) alkyl-(C$_3$-C$_8$) cycloalkyl, —(C$_1$-C$_7$) alkyl-phenyl substituted three times with R2, —C(O)-phenyl substituted three times with R2, —C(O)—(C$_1$-C$_7$) alkyl, —C(O)—(C$_3$-C$_8$) cycloalkyl, —(C$_1$-C$_7$) alkyl-C(O)-phenyl substituted three times with R2, —S—(C$_1$-C$_7$) alkyl, —S—(C$_1$-C$_7$) alkyl-phenyl substituted three times with R2, —S—(C$_3$-C$_8$) cycloalkyl-(C$_1$-C$_7$) alkyl, —S—(C$_3$-C$_8$) cycloalkyl, —S—(C$_2$-C$_7$) alkenyl, —S-phenyl substituted three times with R2, —SO$_2$-phenyl substituted three times with R2, —SO$_2$R7, or —S(O)R7.
5. The compound or salt of claim 2 wherein R1 is —CN, —NO$_2$, —(C$_1$-C7) alkyl, —(C$_3$-C$_8$) cycloalkyl, —(C$_1$-C$_7$) alkyl-S(O)$_2$—(C$_1$-C$_3$) alkyl, —(C$_1$-C$_7$) alkyl-C(O)—O—R3, —(C$_1$-C$_7$) alkyl-S(O)$_2$-phenyl substituted three times with R2, —(C$_1$-C$_7$) alkyl-S—(C$_1$-C$_7$) alkyl, —(C$_1$-C$_7$) alkyl-(C$_3$-C$_8$) cycloalkyl, —(C$_1$-C$_7$) alkyl-phenyl substituted three times with R2, —C(O)—phenyl substituted three times with R2, —C(O)—(C$_1$-C$_7$) alkyl, —C(O)—(C$_3$-C$_8$) cycloalkyl, or —(C1-C7) alkyl-C(O)-phenyl substituted three times with R2.
6. The compound or salt of claim 2 wherein R1 is —S—(C$_1$-C$_7$) alkyl, —S—(C$_1$-C$_7$) alkyl-phenyl substituted three times with R2, —S—(C$_3$-C$_8$) cycloalkyl-(C$_1$-C$_7$) alkyl, —S—(C₃-C₈) cycloalkyl, —S—(C₂-C₇) alkenyl, —S-phenyl substituted three times with R2, —SO₂-phenyl substituted three times with R2, —SO₂R7, or —S(O)R7.

7. The compound or salt of claim 2 wherein one independent occurrence of R2 is —H, -halogen, —(C₁-C₇) alkyl, —C(O)R7, —C(O)OR7, —C(O)(C₃-C₈)cycloalkyl, —OCF₃, —OR7, —SR7, —SO₂R7, —SO₂CF₃, or —S(O)R7, and a second independent occurrence of R2 is —H, -halogen, or —(C1-C7) alkyl, and a third independent occurrence of R2 is —H or-halogen.

8. The compound or salt of claim 2 wherein one independent occurrence of R2 is SO₂R7, —SO₂CF₃, or —S(O)R7, and a second independent occurrence of R2 is —H, halogen, or —(C₁-C₇) alkyl, and a third independent occurrence of R2 is —H or halogen.

9. The compound or salt of claim 2 wherein one independent occurrence of R6 is —CH₃ and the second independent occurrence of R6 is —H.

10. The compound of claim 1 selected from the group consisting of formulae X1 to X16, X20, X23, X24, X27 to X31:

| Formula Number | Structure |
|---|---|
| X1 | 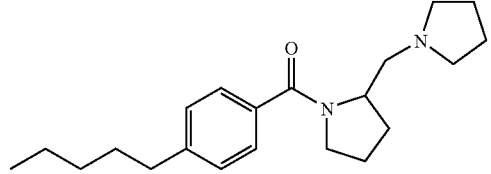 |
| X2 | 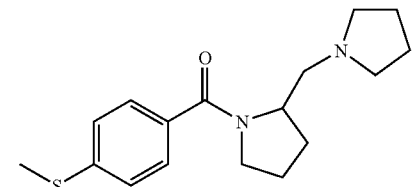 |
| X3 | 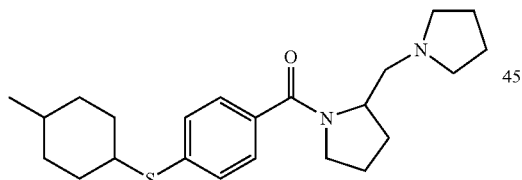 |
| X4 | 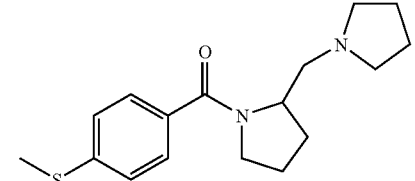 |
| X5 | 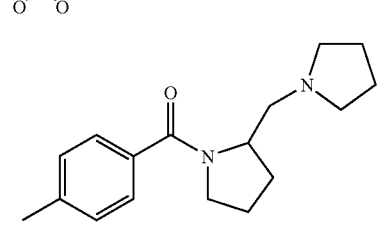 |

-continued

| Formula Number | Structure |
|---|---|
| X6 | 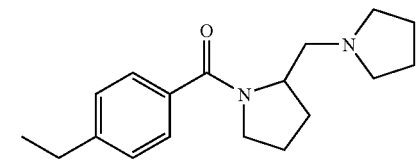 |
| X7 | 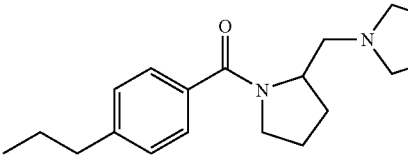 |
| X8 | 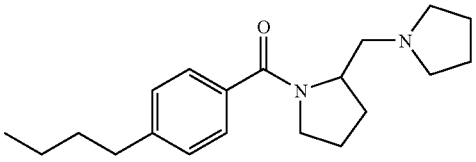 |
| X9 | 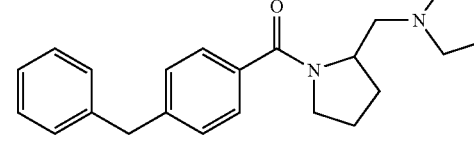 |
| X10 | 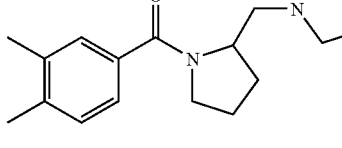 |
| X11 | 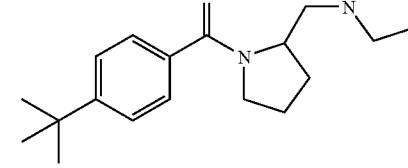 |
| X12 | 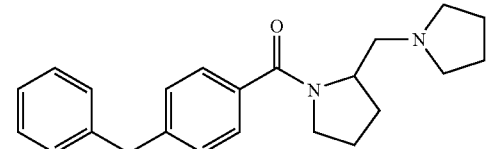 |
| X13 | 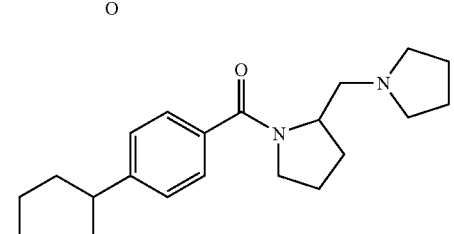 |

| Formula Number | Structure |
|---|---|
| X14 | 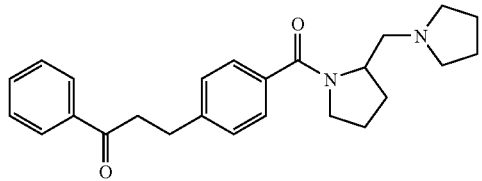 |
| X15 | 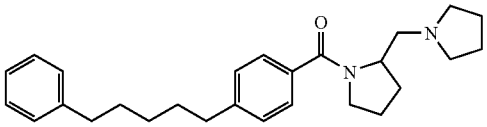 |
| X16 | 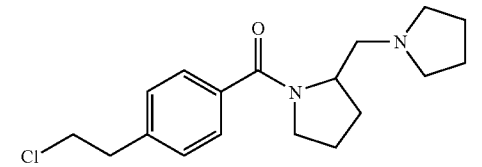 |
| X20 | 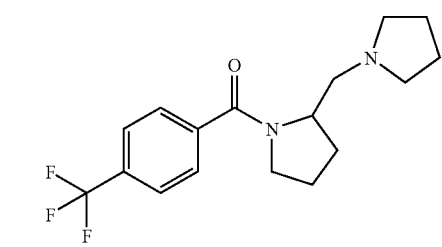 |
| X23 | 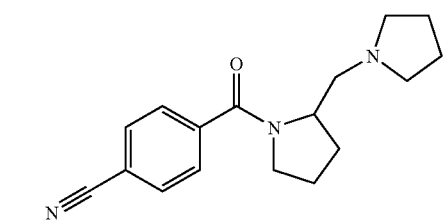 |
| X24 | 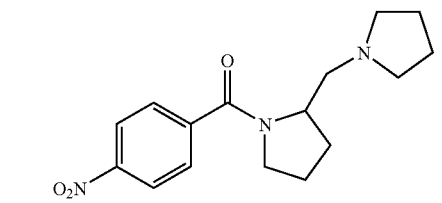 |
| X27 | 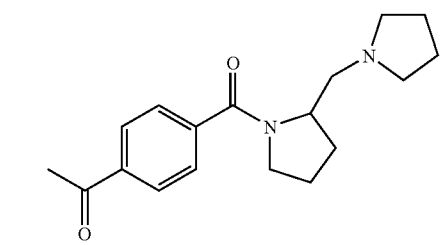 |

| Formula Number | Structure |
|---|---|
| X28 | 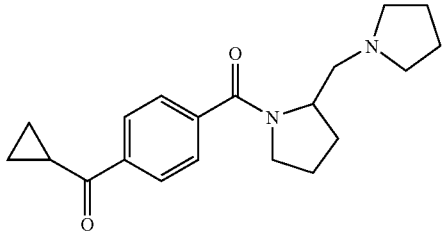 |
| X30 | 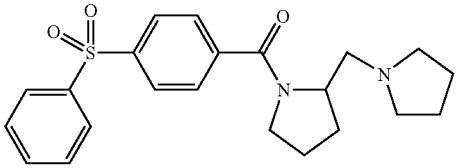 |
| X31 | 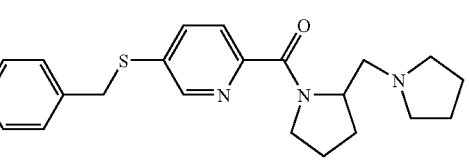 | or a pharmaceutically acceptable salt thereof

11. The compound of claim 1, selected from the group consisting of:
(S)-(4-Pentyl-phenyl)-(2-pyrrolidin-1-ylmethyl-pyrrolidin-1-yl)-methanone,
(S)-(4-Methylsulfanyl-phenyl)-(2-pyrrolidin-1-ylmethyl-pyrrolidin-1-yl)-methanone,
(S)-[4-(4-Methyl-cyclohexylsulfanyl)-phenyl]-(2-pyrrolidin-1 -yl)-methanone,
(S)-(4-Methanesulfonyl-phenyl)-(2-pyrrolidin-1-ylmethyl-pyrrolidin-1-yl)-methanone,
(S)-(2-Pyrrolidin-1-ylmethyl-pyrrolidin-1-yl)-p-tolyl-methanone,
(S)-(4-Ethyl-phenyl)-(2-pyrrolidin-1-ylmethyl-pyrrolidin-1-yl)-methanone,
(S)-(4-Propyl-phenyl)-(2-pyrrolidin-1-ylmethyl-pyrrolidin-1-yl)-methanone,
(S)-(4-Butyl-phenyl)-(2-pyrrolidin-1-ylmethyl-pyrrolidin-1-yl)-methanone,
(S)-(4-Benzyl-phenyl)-(2-pyrrolidin-1-ylmethyl-pyrrolidin-1-yl)-methanone,
(S)-(3,4-Dimethyl-phenyl)-(2-pyrrolidin-1-ylmethyl-pyrrolidin-1-yl)-methanone,
(S)-(4-tert-Butyl-phenyl)-(2-pyrrolidin-1-ylmethyl-pyrrolidin-1-yl)-methanone,
(S)-(4-Benzoyl-phenyl)-(2-pyrrolidin-1-ylmethyl-pyrrolidin-1-yl)-methanone,
(S)-(4-Cyclohexyl-phenyl)-(2-pyrrolidin-1-ylmethyl-pyrrolidin-1-yl)-methanone,
1-Phenyl-3-[4-(2-(S)-pyrrolidin-1-ylmethyl-pyrrolidine-1-carbonyl)-phenyl]-propan-1-one,
[4-(5-Phenyl-pentyl)-phenyl]-(2-(S)-pyrrolidin-1-ylmethyl-pyrrolidin-1-yl)-methanone,
(S)-[4-(2-Chloro-ethyl)-phenyl]-(2-pyrrolidin-1-ylmethyl-pyrrolidin-1-yl)-methanone,
(S)-(2-Pyrrolidin-1-ylmethyl-pyrrolidin-1-yl)-(4-trifluoromethyl-phenyl)-methanone,
4-(2-(S)-Pyrrolidin-1-ylmethyl-pyrrolidine-1-carbonyl)-benzonitrile, (4-Nitro-phenyl)-(2-(S)-pyrrolidin-1-ylmethyl-pyrrolidin-1-yl)-methanone, 1-[4-(2-(S)-Pyrrolidin-1-ylmethyl-pyrrolidine-1-carbonyl)-phenyl]-ethanone, (4-Cyclopropanecarbonyl-phenyl)-(2-(S)-pyrrolidin-1-ylmethyl-pyrrolidin-1-yl)-methanone, (4-Benzenesulfonyl-phenyl)-(2-(S)-pyrrolidin-1-ylmethyl-pyrrolidin-1-yl)-methanone, (5-Benzylsulfanyl-pyridin-2-yl)-(2-(S)-pyrrolidin-1-ylmethyl-pyrrolidin-1-yl)-methanone, (2-(S)-Pyrrolidin-1-ylmethyl-pyrrolidin-1-yl)-(-4-bromo-3-fluoro-phenyl-4-yl)-methanone, and or a pharmaceutically acceptable salt thereof.

12. A pharmaceutical composition which comprises a compound or salt selected from the group consisting of:

(S)-(4-Pentyl-phenyl)-(2-pyrrolidin-1-ylmethyl-pyrrolidin-1-yl)-methanone, (S)-(4-Methylsulfanyl-phenyl)-(2-pyrrolidin-1-ylmethyl-pyrrolidin-1-yl)-methanone, (S)-[4-(4-Methyl-cyclohexylsulfanyl)-phenyl]-(2-pyrrolidin-1-ylmethyl-pyrrolidin-1-yl)-methanone, (S)-(4-Methanesulfonyl-phenyl)-(2-pyrrolidin-1-ylmethyl-pyrrolidin-1-yl)-methanone, (S)-(2-Pyrrolidin-1-ylmethyl-pyrrolidin-1-yl)-p-tolyl-methanone, (S)-(4-Ethyl-phenyl)-(2-pyrrolidin-1-ylmethyl-pyaolidin-1-yl)-methanone, (S)-(4-Propyl-phenyl)-(2-pyrrolidin-1-ylmethyl-pyaolidin-1-yl)-methanone, (S)-(4-Butyl-phenyl)-(2-pyrrolidin-1-ylmethyl-pyrrolidin-1-yl)-methanone, (S)-(4-Benzyl-phenyl)-(2-pyrrolidin-1-ylmethyl-pyrrolidin-1-yl)-methanone, (S)-(3,4-Dimethyl-phenyl)-(2-pyrrolidin-1-ylmethyl-pyrrolidin-1-yl)-methanone, (S)-(4-tert-Butyl-phenyl)-(2-pyrrolidin-1-ylmethyl-pyaolidin-1-yl)-methanone, (S)-(4-Benzoyl-phenyl)-(2-pyrrolidin-1-ylmethyl-pyrrolidin-1-yl)-methanone, (S)-(4-Cyclohexyl-phenyl)-(2-pyrrolidin-1-ylmethyl-pyaolidin-1-yl)-methanone, 1-Phenyl-3-[4-(2-(S)-pyrrolidin-1-ylmethyl-pyrrolidine-1-carbonyl)-phenyl]-propan-1-one,

[4-(5-Phenyl-pentyl)-phenyl]-(2-(S)-pyrrolidin-1-ylmethyl-pyrrolidin-1-yl)-methanone, (S)-[4-(2-Chloro-ethyl)-phenyl]-(2-pyrrolidin-1-ylmethyl-pyrrolidin-1-yl)-methanone, (4-Bromo-2-fluoro-phenyl)-(2-(S)-pyrrolidin-1-ylmethyl-pyrrolidin-yl)methanone, (4-Fluoro-phenyl)-(2-(S)-pyrrolidin-1-ylmethyl-pyrrolidin-1-yl)-methanone, (4-Bromo-2-fluoro-phenyl)-[2-(S)-(2-(R)-methyl-pyrrolidin-1-ylmethyl)-pyrrolidin-1-yl]-methanone, (S)-(2-Pyrrolidin-1-ylmethyl-pyaolidin-1-yl)-(4-trifluoromethyl-phenyl)-methanone, (4-Bromo-phenyl)-(2-(S)-pyrrolidin-1-ylmethyl-pyrrolidin-yl)methanone, (S)-(4-Chloro-phenyl)-(2-pyrrolidin-1-ylmethyl-pyaolidin-1-yl)-methanone, 4-(2-(S)-Pyrrolidin-1-ylmethyl-pyrrolidine-1-carbonyl)-benzonitrile, (4-Nitro-phenyl)-(2-(S)-pyrrolidin-1-ylmethyl-pyaolidin-1-yl)-methanone, (4-Bromo-2-trifluoromethyl-phenyl)-(2-(S)-pyrrolidin-1-ylmethyl-pyaolidin-1-yl)-methanone, 1-[4-(2-(S)-Pyrrolidin-1-ylmethyl-pyrrolidine-1-carbonyl)-phenyl]-ethanone, (4-Cyclopropanecarbonyl-phenyl)-(2-(S)-pyrrolidin-1-ylmethyl-pyrrolidin-1-yl)-methanone, (4-Benzenesulfonyl-phenyl)-(2-(S)-pyrrolidin-1-ylmethyl-pyrrolidin-1-yl)-methanone, (5-Benzylsulfanyl-pyridin-2-yl)-(2-(S)-pyrrolidin-1-ylmethyl-pyaolidin-1-yl)-methanone, (2-(S)-Pyrrolidin-1-ylmethyl-pyaolidin-1-yl)-(-4-bromo-3-fluoro-phenyl-4-yl)-methanone, and (4-Bromo-phenyl)-[2-(S)-(2-(R)-Methyl-pyrrolidin-1-ylmethyl)-pyrrolidin-1-yl]-methanone, and a pharmaceutically acceptable carrier.

* * * * *